(12) United States Patent
Li et al.

(10) Patent No.: US 7,994,285 B2
(45) Date of Patent: Aug. 9, 2011

(54) ANTI-NOTCH3 ANTIBODIES

(75) Inventors: Kang Li, San Diego, CA (US); Sek Chung Fung, Houston, TX (US); Zhengbin Yao, Berwyn, PA (US)

(73) Assignee: Genentech, Inc., South San Francisco, CA (US)

( * ) Notice: Subject to any disclaimer, the term of this patent is extended or adjusted under 35 U.S.C. 154(b) by 674 days.

(21) Appl. No.: 11/874,645

(22) Filed: Oct. 18, 2007

(65) Prior Publication Data

US 2008/0131908 A1 Jun. 5, 2008

Related U.S. Application Data

(60) Provisional application No. 60/852,861, filed on Oct. 19, 2006.

(51) Int. Cl.
*C07K 16/28* (2006.01)
*C07K 7/00* (2006.01)
*C07K 14/475* (2006.01)
*C12P 21/00* (2006.01)

(52) U.S. Cl. ............... 530/387.1; 530/327; 530/328; 530/329; 530/350; 530/387.3; 530/388.22; 530/391.3

(58) Field of Classification Search .................. None
See application file for complete search history.

(56) References Cited

U.S. PATENT DOCUMENTS

| | | | |
|---|---|---|---|
| 5,648,464 | A | 7/1997 | Artavanis-Tsakonas et al. |
| 5,780,300 | A | 7/1998 | Artavanis-Tsakonas et al. |
| 5,786,158 | A | 7/1998 | Artavanis-Tsakonas et al. |
| 5,789,195 | A | 8/1998 | Artavanis-Tsakonas et al. |
| 6,083,904 | A | 7/2000 | Artavanis-Tsakonas et al. |
| 6,090,922 | A | 7/2000 | Artavanis-Tsakonas et al. |
| 6,149,902 | A | 11/2000 | Artavanis-Tsakonas et al. |
| 6,436,650 | B1 | 8/2002 | Artavanis-Tsakonas et al. |
| 6,692,919 | B1 | 2/2004 | Artavanis-Tsakonas et al. |
| 2002/0151487 | A1 | 10/2002 | Nickoloff et al. |
| 2003/0186290 | A1 | 10/2003 | Tournier-Lasserve et al. |
| 2004/0058443 | A1 | 3/2004 | Artavanis-Tsakonas et al. |
| 2004/0242482 | A1 | 12/2004 | Gehring et al. |
| 2005/0112121 | A1 | 5/2005 | Artavanis-Tsakonas et al. |
| 2005/0158859 | A1 | 7/2005 | Artavanis-Tsakonas et al. |
| 2005/0208027 | A1 | 9/2005 | Conboy et al. |
| 2006/0002924 | A1 | 1/2006 | Bodmer et al. |
| 2007/0003983 | A1 | 1/2007 | Artavanis-Tsakonas et al. |
| 2008/0107648 | A1 | 5/2008 | Noguera et al. |
| 2008/0118520 | A1 | 5/2008 | Li et al. |
| 2008/0226621 | A1 | 9/2008 | Fung et al. |

FOREIGN PATENT DOCUMENTS

| | | |
|---|---|---|
| FR | 2 777 285 A1 | 10/1999 |
| WO | 95/15982 | 6/1995 |
| WO | 00/20576 | 4/2000 |
| WO | 02/24221 A2 | 3/2002 |
| WO | 2006/015375 A2 | 2/2006 |
| WO | 2006/017173 A1 | 2/2006 |
| WO | 2006/053063 A2 | 5/2006 |
| WO | 2006/068822 A1 | 6/2006 |
| WO | 2008/057144 A2 | 5/2008 |
| WO | 2008/150525 A1 | 11/2008 |

OTHER PUBLICATIONS

Li et al. beta-Endorphin omission analogs: dissociation of immunoreactivity from other biological activities. Proc Natl Acad Sci U S A. 77(6):3211-3214, 1980.*
Lederman et al. A single amino acid substitution in a common African allele of the CD4 molecule ablates binding of the monoclonal antibody, OKT4. Mol Immunol. 28(11):1171-1181, 1991.*
Daniel et al. Virology 202: 540-549, 1994.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Ngo et al. Computational complexity, protein structure prediction, and the Levinthal paradox. The Protein Folding Problem and Tertiary Structure Prediction, pp. 492-495, 1994.*
Wells. J.A. Additivity of mutational effects in proteins. Biochemistry 29 (37): 8509-8517, 1990.*
Davies et al., "Affinity improvement of single antibody VH domains: residues in all three hypervariable regions affect antigen binding" *Immunotechnology* 2:169-179 (1996).
Holt et al., "Domain antibodies: proteins for therapy" *Trends Biotechnol.* 21(11):484-490 (Nov. 2003).
Joutel et al., "Skin biopsy immunostaining with a Notch3 monoclonal antibody for CADASIL diagnosis" *Lancet* 358:2049-2051 (2001).
Jurynczyk et al., "Notch3 Inhibition in Myelin-Reactive T Cells Down-Regulates Protein Kinase Cθ and Attenuates Experimental Autoimmune Encephalomyelitis" *Journal of Immunology* 180(4):2634-2640 (2008).
Li et al., "Modulation of Notch Signaling by Antibodies Specific for the Extracellular Negative Regulatory Region of NOTCH3" *Journal of Biological Chemistry* 283(12):8046-8054 (Mar. 21, 2008).
PCT International Search Report mailed Dec. 23, 2008, in counterpart PCT Application No. PCT/US2007/081799, filed Oct. 18, 2007.
Allenspach et al., "Notch signaling in cancer" *Cancer Biol Ther.* 1(5):466-76 (2002).
Anastasi et al., "Expression of activated Notch3 in transgenic mice enhances generation of T regulatory cells and protects against experimental autoimmune diabetes" *J Immunol.* 171(9):4504-11 (Nov. 2003).

(Continued)

*Primary Examiner* — Bridget E Bunner
(74) *Attorney, Agent, or Firm* — Danielle M. Pasqualone

(57) ABSTRACT

The present invention relates to novel antibodies that bind specifically to human Notch 3 and their use in the detection and/or diagnosis of Notch 3 related diseases, such as cancer. The present invention also includes nucleic acids encoding these novel antibodies, vectors and cell lines harboring the nucleic acids, and kits comprising the antibodies for use in the detection and diagnosis.

9 Claims, 4 Drawing Sheets

OTHER PUBLICATIONS

Androutsellis-Theotokis et al., "Notch signalling regulates stem cell numbers in vitro and in vivo" *Nature* 442:823-6 (Aug. 2006).
Artavanis-Tsakonas et al., "Notch Signaling" *Science* 268:225-232 (Apr. 14, 1995).
Artavanis-Tsakonas et al., "Notch Signaling: Cell Fate Control and Signal Integration in Development" *Science* 284:770-776 (1999).
Aster et al., "The folding and structural integrity of the first LIN-12 module of human Notch1 are calcium-dependent" *Biochemistry* 38(15):4736-42 (Apr. 1999).
Bellavia et al., "Combined expression of pTalpha and Notch3 in T cell leukemia identifies the requirement of preTCR for leukemogenesis" *Proc Natl Acad Sci U S A.* 99(5):3788-93 (Mar. 2002).
Bocchetta et al., "Notch-1 induction, a novel activity of SV40 required for growth of SV40-transformed human mesothelial cells" *Oncogene* 22(1):81-9 (Jan. 2003).
Bolos et al., "Notch signaling in development and cancer" *Endocr Rev.* 28(3):339-63 (May 2007).
Bray, "Notch signalling: a simple pathway becomes complex" *Nat Rev Mol Cell Biol.* 7(9):678-89 (Sep. 2006).
Buchler et al., "The Notch signaling pathway is related to neurovascular progression of pancreatic cancer" *Ann Surg.* 242(6):791-800 (Dec. 2005).
Chiba, "Notch signaling in stem cell systems" *Stem Cells* 24(11):2437-47 (Nov. 2006).
Coffman et al., "Expression of an extracellular deletion of Xotch diverts cell fate in *Xenopus* embryos" *Cell* 73(4):659-71 (May 1993).
Domenga et al., "Notch3 is required for arterial identity and maturation of vascular smooth muscle cells" *Genes Dev.* 18(22):2730-5 (Nov. 2004).
Ellisen et al., "TAN-1, the human homolog of the *Drosophila* notch gene, is broken by chromosomal translocations in T lymphoblastic neoplasms" *Cell* 66(4):649-61 (Aug. 1991).
Fan et al., "Notch pathway inhibition depletes stem-like cells and blocks engraftment in embryonal brain tumors" *Cancer Research* 66(15):7445-52 (Aug. 2006).
Flynn et al., "The role of Notch receptor expression in bile duct development and disease" *J Pathol.* 204(1):55-64 (Sep. 2004).
Fre et al., "Notch signals control the fate of immature progenitor cells in the intestine" *Nature* 435:964-8 (Jun. 2005).
Gordon et al., "Structural basis for autoinhibition of Notch" *Nat Struct Mol Biol.* 14(4):295-300 (Apr. 2007).
Haruki et al., "Dominant-negative Notch3 receptor inhibits mitogen-activated protein kinase pathway and the growth of human lung cancers" *Cancer Research* 65(9):3555-61 (May 2005).
Hedvat et al., "Insights into extramedullary tumour cell growth revealed by expression profiling of human plasmacytomas and multiple myeloma" *Br J Haematol.* 122(5):728-44 (Sep. 2003).
Heller et al., "Amino Acids at the Site of V.-J. Recombination Not Encoded by Germline Sequences" *Journal of Experimental Medicine* 166:637-646 (1987).
Houde et al., "Overexpression of the NOTCH ligand JAG2 in malignant plasma cells from multiple myeloma patients and cell lines" *Blood* 104(12):3697-704 (Dec. 2004).
Hu et al., "Overexpression of activated murine Notch1 and Notch3 in transgenic mice blocks mammary gland development and induces mammary tumors" *Am J Pathol.* 168(3):973-90 (Mar. 2006).
Jang et al., "Notch signaling as a target in multimodality cancer therapy" *Curr Opin Mol Ther.* 2(1):55-65 (Feb. 2000).
Joutel et al., "Notch signalling pathway and human diseases" *Semin Cell Dev Biol.* 9(6):619-25 (Dec. 1998).
Joutel et al., "Notch3 mutations in CADASIL, a hereditary adult-onset condition causing stroke and dementia" *Nature* 383:707-10 (Oct. 1996).
Jundt et al., "Jagged1-induced Notch signaling drives proliferation of multiple myeloma cells" *Blood* 103(9):3511-5 (May 2004).
Kadesch, "Notch signaling: a dance of proteins changing partners" *Exp Cell Res.* 260(1):1-8 (Oct. 2000).
Kidd et al., "Sequence of the notch locus of *Drosophila melanogaster*: relationship of the encoded protein to mammalian clotting and growth factors" *Mol Cell Biol.* 6(9):3094-108 (Sep. 1986).
Kopczynski et al., "Delta, a *Drosophila* neurogenic gene, is transcriptionally complex and encodes a protein related to blood coagulation factors and epidermal growth factor of vertebrates" *Genes Dev.* 2:1723-35 (1988).
Leong et al., "Recent insights into the role of Notch signaling in tumorigenesis" *Blood* 107(6):2223-33 (Mar. 2006).
Lu et al., "Selection of potential markers for epithelial ovarian cancer with gene expression arrays and recursive descent partition analysis" *Clin Cancer Res.* 10(10):3291-300 (May 2004).
Mailhos et al., "Delta4, an Endothelial Specific Notch Ligand Expressed at Sites of Physiological and Tumor Angiogenesis" *Differentiation* 69:135-144 (2001).
Malecki et al., "Leukemia-associated mutations within the NOTCH1 heterodimerization domain fall into at least two distinct mechanistic classes" *Mol Cell Biol.* 26(12):4642-51 (Jun. 2006).
Nam at al., "Notch signaling as a therapeutic target" *Curr Opin Chem Biol.* 6(4):501-9 (Aug. 2002).
Park et al., "Notch3 gene amplification in ovarian cancer" *Cancer Research* 66(12):6312-8 (Jun. 2006).
Rao et al., "K Chain Variable Regions from Three Galactan Binding Myeloma Proteins" *Biochemistry* 17(25):5555-5559 (1978).
Reya et al., "Stem cells, cancer, and cancer stem cells" *Nature* 414:105-11 (2001).
Rudikoff et al., "K chain joining segments and structural diversity of antibody combining sites" *Natl. Acad. Sci. USA* 77(7):4270-4274 (1980).
Sanchez-Irizarry at al., "Notch subunit heterodimerization and prevention of ligand-independent proteolytic activation depend, respectively, on a novel domain and the LNR repeats" *Mol Cell Biol.* 24(21):9265-73 (2004).
Screpanti et al., "Notch, a unifying target in T-cell acute lymphoblastic leukemia?" *Trends Mol Med.* 9(1):30-5 (Jan. 2003).
Shimizu et al., "Physical interaction of Delta1, Jagged1, and Jagged2 with Notch1 and Notch3 receptors" *Biochem Biophys Res Commun.* 276(1):385-9 (Sep. 2000).
Sullivan and Bicknell, "New molecular pathways in angiogenesis" *British Journal of Cancer* 89(2):228-231 (Jul. 21, 2003).
Sweeney et al., "Notch 1 and 3 receptor signaling modulates vascular smooth muscle cell growth, apoptosis, and migration via a CBF-1/RBP-Jk dependent pathway" *FASEB J.* 18(12):1421-3 (Sep. 2004).
Swiatek et al., "Notch1 is essential for postimplantation development in mice" *Genes Dev.* 8(6):707-19 (Mar. 1994).
Taichman et al., "Notch1 and Jagged1 expression by the developing pulmonary vasculature" *Dev Dyn.* 225(2):166-75 (Oct. 2002).
Thelu et al., "Notch signalling is linked to epidermal cell differentiation level in basal cell carcinoma, psoriasis and wound healing" *BMC Dermatol.* 2:7 (Apr. 2002).
Vacca et al., "Notch3 and pre-TCR interaction unveils distinct NF-kappaB pathways in T-cell development and leukemia" *EMBO Journal* 25(5):1000-8 (Mar. 2006).
van Es et al., "Notch/gamma-secretase inhibition turns proliferative cells in intestinal crypts and adenomas into goblet cells" *Nature* 435:959-63 (Jun. 2005).
van Limpt et al., "Phox2B mutations and the Delta-Notch pathway in neuroblastoma" *Cancer Lett.* 228:59-63 (Oct. 2005).
Vardar et al., "Nuclear magnetic resonance structure of a prototype Lin12-Notch repeat module from human Notch1" *Biochemistry* 42(23):7061-7 (Jun. 2003).
Von Boehmer, "Notch in lymphopoiesis and T cell polarization" *Nat Immunol.* 6(7):641-2 (Jul. 2005).
Weijzen et al., "Activation of Notch-1 signaling maintains the neoplastic phenotype in human Ras-transformed cells" *Nat Med.* 8(9):979-986 (Sep. 2002).

Weng et al., "Activating mutations of NOTCH1 in human T cell acute lymphoblastic leukemia" *Science* 306(5694):269-271 (Oct. 8, 2004).

Wharton et al., "Nucleotide sequence from the neurogenic locus notch implies a gene product that shares homology with proteins containing EGF-like repeats" *Cell* 43:567-81 (Dec. 1985).

Xu et al., "Regions of *Drosophila* Notch that contribute to ligand binding and the modulatory influence of Fringe" *J Biol Chem.* 280(34):30158-65 (Aug. 2005).

Yabe et al., "Immunohistological localization of Notch receptors and their ligands Delta and Jagged in synovial tissues of rheumatoid arthritis" *J Orthop Sci.* 10(6):589-94 (Nov. 2005).

Yochem et al., "The *Caenorhabditis elegans* lin-12 gene encodes a transmembrane protein with overall similarity to *Drosophila* Notch" *Nature* 335:547-50 (Oct. 1988).

Zeng et al., "Crosstalk between tumor and endothelial cells promotes tumor angiogenesis by MAPK activation of Notch signaling" *Cancer Cell* 8(1):13-23 (Jul. 2005).

Zweidler-McKay et al., "Notch signaling is a potent inducer of growth arrest and apoptosis in a wide range of B-cell malignancies" *Blood* 106(12):3898-906 (Dec. 2005).

\* cited by examiner

FIGURE 1:

Amino Acid Sequence of Human Notch 3  (NP_ 000426)

```
   1 MGPGARGRRR RRRPMSPPPP PPPVRALPLL LLLAGPGAAA PPCLDGSPCA NGGRCTQLPS
  61 REAACLCPPG WVGERCQLED PCHSGPCAGR GVCQSSVVAG TARFSCRCPR GFRGPDCSLP
 121 DPCLSSPCAH GARCSVGPDG RFLCSCPPGY QGRSCRSDVD ECRVGEPCRH GGTCLNTPGS
 181 FRCQCPAGYT GPLCENPAVP CAPSPCRNGG TCRQSGDLTY DCACLPGFEG QNCEVNVDDC
 241 PGHRCLNGGT CVDGVNTYNC QCPPEWTGQF CTEDVDECQL QPNACHNGGT CFNTLGGHSC
 301 VCVNGWTGES CSQNIDDCAT AVCFHGATCH DRVASFYCAC PMGKTGLLCH LDDACVSNPC
 361 HEDAICDTNP VNGRAICTCP PGFTGGACDQ DVDECSIGAN PCEHLGRCVN TQGSFLCQCG
 421 RGYTGPRCET DVNECLSGPC RNQATCLDRI GQFTCICMAG FTGTYCEVDI DECQSSPCVN
 481 GGVCKDRVNG FSCTCPSGFS GSTCQLDVDE CASTPCRNGA KCVDQPDGYE CRCAEGFEGT
 541 LCDRNVDDCS PDPCHHGRCV DGIASFSCAC APGYTGTRCE SQVDECRSQP CRHGGKCLDL
 601 VDKYLCRCPS GTTGVNCEVN IDDCASNPCT FGVCRDGINR YDCVCQPGFT GPLCNVEINE
 661 CASSPCGEGG SCVDGENGFR CLCPPGSLPP LCLPPSHPCA HEPCSHGICY DAPGGFRCVC
 721 EPGWSGPRCS QSLARDACES QPCRAGGTCS SDGMGFHCTC PPGVQGRQCE LLSPCTPNPC
 781 EHGGRCESAP GQLPVCSCPQ GWQGPRCQQD VDECAGPAPC GPHGICTNLA GSFSCTCHGG
 841 YTGPSCDQDI NDCDPNPCLN GGSCQDGVGS FSCSCLPGFA GPRCARDVDE CLSNPCGPGT
 901 CTDHVASFTC TCPPGYGGFH CEQDLPDCSP SSCFNGGTCV DGVNSFSCLC RPGYTGAHCQ
 961 HEADPCLSRP CLHGGVCSAA HPGFRCTCLE SFTGPQCQTL VDWCSRQPCQ NGGRCVQTGA
1021 YCLCPPGWSG RLCDIRSLPC REAAAQIGVR LEQLCQAGGQ CVDEDSSHYC VCPEGRTGSH
1081 CEQEVDPCLA QPCQHGGTCR GYMGGYMCEC LPGYNGDNCE DDVDECASQP CQHGGSCIDL
1141 VARYLCSCPP GTLGVLCEIN EDDCGPGPPL DSGPRCLHNG TCVDLVGGFR CTCPPGYTGL
1201 RCEADINECR SGACHAAHTR DCLQDPGGGF RCLCHAGFSG PRCQTVLSPC ESQPCQHGGQ
1261 CRPSPGPGGG LIFTCHCAQP FWGPRCERVA RSCRELQCPV GVPCQQIPRG PRCACPPGLS
1321 GPSCRSFPGS PPGASNASCA AAPCLHGGSC RPAPLAPFFR CACAQGWTGP RCEAPAAAPE
1381 VSEEPRCPRA ACQAKRGDQR CDRECNSPGC GWDGGDCSLS VGDPWRQCEA LQCWRLFNNS
1441 RCDPACSSPA CLYDNFDCHA GGRERTCNPV YEKYCADHFA DGRCDQGCNT EECGWDGLDC
1501 ASEVPALLAR GVLVLTVLLP PEELLRSSAD FLQRLSAILR TSLRFRLDAH GQAMVFPYHR
1561 PSPGSEPRAR RELAPEVIGS VVMLEIDNRL CLQSPENDHC FPDAQSAADY LGALSAVERL
1621 DFPYPLRDVR GEPLEPPEPS VPLLPLLVAG AVLLLVILVL GVMVARRKRE HSTLWFPEGF
1681 SLHKDVASGH KGRREPVGQD ALGMKNMAKG ESLMGEVATD WMDTECPEAK RLKVEEPGMG
1741 AEEAVDCRQW TQHHLVAADI RVAPAMALTP PQGDADADGM DVNVRGPDGF TPLMLASFCG
1801 GALEPMPTEE DEADDTSASI ISDLICQGAQ LGARTDRTGE TALHLAARYA RADAAKRLLD
1861 AGADTNAQDH SGRTPLHTAV TADAQGVFQI LIRNRSTDLD ARMADGSTAL ILAARLAVEG
1921 MVEELIASHA DVNAVDELGK SALHWAAAVN NVEATLALLK NGANKDMQDS KEETPLFLAA
1981 REGSYEAAKL LLDHFANREI TDHLDRLPRD VAQERLHQDI VRLLDQPSGP RSPPGPHGLG
2041 PLLCPPGAFL PGLKAAQSGS KKSRRPPGKA GLGPQGPRGR GKKLTLACPG PLADSSVTLS
2101 PVDSLDSPRP FGGPPASPGG FPLEGPYAAA TATAVSLAQL GGPGRAGLGR QPPGGCVLSL
2161 GLLNPVAVPL DWARLPPPAP PGPSFLLPLA PGPQLLNPGT PVSPQERPPP YLAVPGHGEE
2221 YPVAGAHSSP PKARFLRVPS EHPYLTPSPE SPEHWASPSP PSLSDWSEST PSPATATGAM
2281 ATTTGALPAQ PLPLSVPSSL AQAQTQLGPQ PEVTPKRQVL A  (SEQ ID NO 1)
```

FIGURE 2A mAb 255A-71 heavy chain variable region sequence:

SDVQLQESGPGLVKPSQSLSLTCSVT<u>GYSITSGYYWN</u>WIRQFPGNKLEWMG<u>FISYDGSNNYN</u>
                               CDR-H1                            CDR-H2

<u>PSLKNRI</u>SITRDTSKNQFFLKLNSVTTEDTATFYCAT<u>LYYDYDGNYFDY</u>WGQGTTLTVSSA
                                         CDR-H3

(SEQ ID NO: 2)

FIGURE 2B mAb 255A-71 light chain (kappa) variable region sequence

CDIQMTQTTSSLSASLGDRVTISC<u>RTSQDISNYLN</u>WYQQKPDGTVKLLIY<u>YTSRLHS</u>GVPSR
                         CDR-L1                       CDR-L2
FSGSGSGTDYSLTISNLEQEDIATYFC<u>QQGNALPLT</u>FGPGTKLELKRADAAPTV
                             CDR-L3

(SEQ ID NO: 3)

FIGURE 3A mAb 255A-77 heavy chain variable region sequence

CQVQLQQSGDDLVKPGASVKLSCKAS<u>GYTFTSYWIN</u>WIKQRPGQGLEWIG<u>HIGPGSGSTYYN</u>
            CDR-H1          CDR-H2
<u>EIFKG</u>KATLTVDTSSSTAYIQLSSLSSEDSAVYFCVL<u>TRYFYAMDY</u>WGQGTSVTVSSA
                   CDR-H3

(SEQ ID NO: 4)

FIGURE 3B mAb 255A-77 light chain (kappa) variable region sequence

DIVMTQSPSSLAVTAGEKVTMRC<u>KSSQSLLWSVNQNNYLS</u>WYQQKQGQPPKLLIY<u>GASIRES</u>
          CDR-L1            CDR-L2
WVPDRFTGSGSGTDFTLTISNVHVEDLAVYYC<u>QHNHGSFLPLT</u>FGAGTKLELKRADAAPTV
               CDR-L3

(SEQ ID NO: 5)

FIGURE 4A mAb 256A-13 heavy chain variable region sequence

SQVQLQQSGAELAKPGTSVKMACKASGYTFTTHWMNWVKQRPGQGLEWIGTINPSNDFTDCN
                          CDR-H1                    CDR-H2

QKFKDKAILTADKSSSTAYMQLSSLTSEDSAIYYCASGLTARAWFAYWGQGTLVTVSAA
                                      CDR-H3

(SEQ ID NO: 6)

FIGURE 4B mAb 256A-13 light chain (kappa) variable region sequence

RATISCRASQSVTTSNYSYMHWFQQKPGQPPKLLIKYASNLDSGVPARFSGSGSGTDFTLNI
      CDR-L1                        CDR-L2
HPVEEEDTATFYCQHSWEIPYTFGGGTNLEIKRADAAPTV    (SEQ ID NO: 7)
              CDR-L3

ANTI-NOTCH3 ANTIBODIES

CROSS-REFERENCE TO RELATED APPLICATIONS

This application claims the benefit of U.S. Provisional Application No. 60/852,861, filed Oct. 19, 2006, the disclosure of which is incorporated herein by reference in its entirety.

FIELD OF THE INVENTION

The present invention relates to novel anti-Notch 3 antibodies and their use in the detection of Notch 3 in a sample and/or diagnosis of a Notch-3 related disease or disorder.

BACKGROUND OF THE INVENTION

The Notch gene was first described in 1917 when a strain of the fruit fly Drosophila melanogaster was found to have notched wing blades (Morgan, Am Nat 51:513 (1917)). The gene was cloned some seventy years later and turned out to be a cell surface receptor playing a key role in the development of many different cell types and tissues (Wharton et al., Cell 43:567-581 (1985)). Since then, the gene and its molecular mechanisms have been extensively studied. The generality of the Notch pathway manifests itself at different levels. At the genetic level, many mutations exist that affect the development of a very broad spectrum of cell types in Drosophila.

The Notch signaling pathway was soon found to be an evolutionarily conserved signaling mechanism from Drosophila to vertebrates and has been found to be involved in many cellular processes, such as differentiation, cell fate decisions, maintenance of stem cells, proliferation, and apoptosis, in various cell types during and after development (See review Artavanis, et al., Science 268:225 (1995)). Knockout mutations were found to be lethal in embryonic mice, consistent with lymphoblastic leukemia (Ellisen, et al., Cell 66(4):649-661 (1991)). The expression of mutant forms of Notch in developing Xenopus embryos interfere profoundly with normal development (Coffman, et al., Cell 73 (1993)). In humans, there have been several genetic diseases linked to Notch mutations (Artavanis-Tsakonas, et al. Science 284: 770-776 (1999)).

Mammals possess four Notch proteins (designated Notch1 to 4) and five corresponding ligands (Delta-1, -3, and -4, and Jagged-1 and -2). The mammalian Notch gene encodes a ~300 kd protein that is cleaved during its transport to the cell surface and consequently exists as a heterodimer. The extracellular portion has many epidermal growth factor (EGF)-like repeats followed by three cysteine-rich Notch/Lin12 repeats (LNk) (Wharton, et al., Cell 43:567 (1985); Kidd, et al., Mol Cell Biol 6:3431 (1986); Kopczynski, et al., Genes Dev 2:1723 (1988); Yochem, et al., Nature 335:547 (1988)). The amino-terminal EGF-like repeats participate in ligand binding, whereas the Lin 12 repeats prevent signaling in the absence of ligand. The signal induced by ligand binding is transmitted to the nucleus by a process involving proteolytic cleavage of the receptor and nuclear translocation of the intracellular domain (Notch-IC). After entering the nucleus, Notch-IC competes with inhibitory proteins and recruits coactivators, including mastermind-like (MAML) proteins, and acetyltransferases. The Notch-IC complex then binds to a transcription factor RBP-J to convert it from a transcriptional repressor to an activator. The few transcriptional factors identified so far vary in their nature and effects on the cell.

Cells in pathological states often express target antigens on their surface that are present in higher concentrations than on their normal counterparts. The use of monoclonal antibodies to identify the presence of these disease markers is attractive because of their high specificities. Notch receptors have been linked to wide range of diseases, such as cancer, neurological disorders, and immune diseases, as reflected by its broad spectrum of activities in humans (Joutel, et al. Cell & Dev Biol 9:619 (1998); Nam, et al., Curr Opin Chem Biol 6:501 (2002)). Many expression studies of Notch proteins in human tissues and cell lines have been reported. For example, increased levels of Notch3 expression is found in many malignant tissues in humans. In leukemia, genetic and biochemical evidence show that Notch3 triggers multiple NF-kappaB activation pathways, which regulates distinct gene clusters involved in either cell differentitation or proliferation and leukemogenesis (Vacca, et al., EMBO J 25:1000 (2006)). Notch3 is also expressed in a subset of neuroblastoma cell lines and serves as a marker for this type of tumor that has constitutional or tumor-specific mutations in the homeobox gene Phox2B, which controls part of the differentiation program of the sympathetic nervous system (van Limpt, et al., Cancer Lett 228:59 (2005)).

Notch3 is also found to be very important in the diagnosis of ovarian cancer. Advanced-stage epithelial ovarian cancer has a poor prognosis with a long-term survival in less than 30% of patients, whereas more than 90% of patients can be cured by conventional therapy when the disease is detected in stage I. No single marker is upregulated and shed in adequate amounts in early stages. Lu and colleagues screened the gene expression of 41,441 known genes and expressed sequence tags between five pools of normal ovarian surface epithelial cells and 42 epithelial ovarian cancers of different stages, grades, and histotypes to identify tumor markers (Clin Cancer Res 10:3291 (2004)). The study found four markers that were 3-fold upregulated and were able to distinguish all tumor samples from normal ovarian surface epithelial cells; one of these genes is Notch3. Other studies have also found that Notch3 expression is upregulated in a series of plasma cell neoplasm, including multiple myeloma, plasma cell leukemia, and extramedullary plasmacytoma (Hedvat, et al., Br J Haematol 122:728 (2003); pancreatic cancer (Buchler, et al., Ann Surg 242:791 (2005)); and T cell acute lymphoblastic leukemias (T-ALL) (Bellavia, et al., Proc Natl Acad Sci USA 99:3788 (2002); Screpanti, et al., Trends Mol Med 9:30 (2003)).

Also, CADASIL (cerebral autosomal dominant arteriopathy with subcortical infarcts and leukoencephalopathy) causes a type of stroke and dementia whose key features include recurrent subcortical ischaemic events and vascular dementia. CADASIL has been found to be associated with a mutant gene localized to chromosome 19 (Joutel, et al., Nature 383:707 (1996)). Joutel et al. identified mutations in CADASIL patients that cause serious disruption of the Notch 3 gene, indicating that Notch3 could be the defective protein in CADASIL patients. Unfortunately, this highly incapacitating and often lethal disease has remained largely undiagnosed or misdiagnosed as multiple sclerosis and Alzheimer's disease. Current studies would tend to demonstrate that it is a condition that is much more widespread than first thought. Efforts have been made to identify diagnostic tools for the disease and develop a therapy.

An additional example of a Notch 3 related disease is familial hemiplegic migraine (FHM), the dominant autosomal form of migraine with aura, located in the same region of chromosome 19 as the Notch3 gene. It should be noted that more than 30% of patients suffering from CADASIL also suffer from migraine with aura. However, the latter is observed in only about 5% of the population and this observation led to the discovery of Notch3 gene involvement in the mechanism of this condition. Similarly, familial paroxytic ataxia has been linked to a gene located in the same region of chromosome 19 and implicating Notch3 in this condition. Other conditions and diseases that have been linked to Notch3 include diabetes (Anastasi, et al., *J Immunol* 171:4504 (2003), rheumatoid arthritis (Yabe, et al., *J Orthop Sci* 10:589 (2005)), disease states in which vascular cell fate occur in vivo (Sweeney, et al., *FASEB J* 18:1421 (2004)), and Alagille syndrome (Flynn, et al., *J Pathol* 204:55 (2004)).

U.S. Pat. No. 5,786,158 describes diagnostic methods and compositions for the detection of malignancy or nervous system disorders based on the level of Notch proteins or nucleic acids. U.S. Application No. 20020151487 describes a diagnostic test to determine the expression levels of Notch ligands, receptors, or other Notch signaling compounds in cells.

Ongoing research studies are currently being pursued to identify other diseases and conditions linked to Notch3 expression. In view of the large number of human diseases associated with the Notch 3 signaling pathway, it is critical that new ways of detecting and diagnosing these diseases be identified. The current invention provides novel anti-Notch 3 antibodies useful for this unmet medical need.

SUMMARY OF THE INVENTION

The present invention provides novel antibodies and fragments thereof useful in the detection and diagnosis of Notch-3 related diseases or disorders.

One aspect of the invention relates to the nucleotide and amino acid sequences of these novel antibodies. Also included are vectors encoding such antibodies and cell lines harboring such vectors.

Another aspect of the invention relates to the use of these antibodies in methods or assays for detecting Notch 3 activation or expression in patients suspected of having a Notch-3 related disease or disorder. Such diseases or disorders may include, but not limited to, cerebral autosomal dominant arteriopathy with subcortical infarcts and leukoencephalopathy (CADASIL), T-cell acute lymphoblastic leukemia, lymphoma, Alagille syndrome, liver disease involving aberrant vasularization; diabetes, ovarian cancer, diseases involving vascular cell fate, rheumatoid arthritis, pancreatic cancer, plasma cell neoplasms (such as multiple myeloma, plasma cell leukemia, and extramedullary plasmacytoma), and neuroblastoma.

Another aspect of the invention relates to the screening of a patient suspected of having a Notch3 related disease or condition to determine if such a patient would benefit from treatment with an anti-Notch 3 antibody. Such detection includes both cell surface detection as well as soluble Notch3 found in the serum of said patient.

BRIEF DESCRIPTION OF THE DRAWINGS

FIG. 1 depicts the amino acid sequence of human Notch 3. The EGF repeat region extends from amino acid residue 43 to 1383 and is indicated by an underline; the LIN12 domain extends from amino acid residue 1384 to 1503 as indicated by bold italics; the Dimerization domain extends from amino acid residue 1504 to 1640 as indicated by a box.

FIG. 2A depicts the heavy chain variable region sequence of anti-Notch 3 monoclonal antibody mAb 255-71 (SEQ ID NO: 2).

FIG. 2B depicts the light chain (kappa) variable region sequence of mAb 255A-71 (SEQ ID NO: 3).

FIG. 3A depicts the heavy chain variable region sequence of anti-Notch 3 monoclonal antibody mAb 255A-77 (SEQ ID NO: 4).

FIG. 3B depicts the light chain (kappa) variable region sequence of mAb 255A-77(SEQ ID NO: 5).

FIG. 4A depicts the heavy chain variable region sequence of anti-Notch 3 monoclonal antibody mAb 256A-13 (SEQ ID NO: 6).

FIG. 4B depicts the light chain (kappa) variable region sequence of mAb 256A-13 (SEQ ID NO: 7).

DETAILED DESCRIPTION

This invention is not limited to the particular methodology, protocols, cell lines, vectors, or reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise, e.g., reference to "a host cell" includes a plurality of such host cells. Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

All patents and publications mentioned herein are incorporated herein by reference to the extent allowed by law for the purpose of describing and disclosing the proteins, enzymes, vectors, host cells, and methodologies reported therein that might be used with the present invention. However, nothing herein is to be construed as an admission that the invention is not entitled to antedate such disclosure by virtue.

DEFINITIONS

Terms used throughout this application are to be construed with ordinary and typical meaning to those of ordinary skill in the art. However, Applicants desire that the following terms be given the particular definition as defined below.

The phrase "substantially identical" with respect to an antibody chain polypeptide sequence may be construed as an antibody chain exhibiting at least 70%, or 80%, or 90%, or 95% sequence identity to the reference polypeptide sequence. The term with respect to a nucleic acid sequence may be construed as a sequence of nucleotides exhibiting at least about 85%, or 90%, or 95%, or 97% sequence identity to the reference nucleic acid sequence.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (mAb) is meant to include intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue binding than an intact antibody (Wahl, et al., *J Nucl Med* 24:316 (1983)).

As used herein, "anti-Notch3 antibody" means an antibody which binds to human Notch3 in such a manner so as to allow detection, diagnosis, or predetermination of a disease associated with Notch 3 activation and/or expression.

The term "variable" in the context of variable domain of antibodies, refers to the fact that certain portions of the variable domains differ extensively in sequence among antibodies and are used in the binding and specificity of each particular antibody for its particular target. However, the variability is not evenly distributed through the variable domains of antibodies. It is concentrated in three segments called complementarity determining regions (CDRs; i.e., CDR1, CDR2, and CDR3) also known as hypervariable regions both in the light chain and the heavy chain variable domains. The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies (see Kabat, et al. Sequences of Proteins of Immunological Interest, National Institute of Health, Bethesda, Md. (1987)). As used herein, numbering of immunoglobulin amino acid residues is done according to the immunoglobulin amino acid residue numbering system of Kabat, et al., unless otherwise indicated.

The term "antibody fragment" refers to a portion of a full-length antibody, generally the target binding or variable region. Examples of antibody fragments include Fab, Fab', F(ab')$_2$ and Fv fragments. The phrase "functional fragment or analog" of an antibody is a compound having qualitative biological activity in common with a full-length antibody. For example, a functional fragment or analog of an anti-Notch3 antibody is one which can bind to a Notch3 receptor in such a manner so as to prevent or substantially reduce the ability of such molecule from having the ability to bind to its ligands. As used herein, "functional fragment" with respect to antibodies, refers to Fv, F(ab) and F(ab')$_2$ fragments. An "Fv" fragment is the minimum antibody fragment which contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Collectively, the six CDRs confer target binding specificity to the antibody. However, even a single variable domain (or half of an Fv comprising only three CDRs specific for a target) has the ability to recognize and bind target, although at a lower affinity than the entire binding site.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, which the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison, et al., *Proc Natl Acad Sci USA* 81:6851 (1984)). Monoclonal antibodies are highly specific, being directed against a single target site. Furthermore, in contrast to conventional (polyclonal) antibody preparations which typically include different antibodies directed against different determinants (epitopes), each monoclonal antibody is directed against a single determinant on the target. In addition to their specificity, monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies for use with the present invention may be isolated from phage antibody libraries using the well known techniques. The parent monoclonal antibodies to be used in accordance with the present invention may be made by the hybridoma method first described by Kohler, et al., *Nature* 256:495 (1975), or may be made by recombinant methods.

The terms "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included. The "host cells" used in the present invention generally are prokaryotic or eukaryotic hosts.

The term "vector" means a DNA construct containing a DNA sequence which is operably linked to a suitable control sequence capable of effecting the expression of the DNA in a suitable host. The vector may be a plasmid, a phage particle, or simply a potential genomic insert. Once transformed into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the invention is intended to include such other forms of vectors which serve equivalent function as and which are, or become, known in the art.

The word "label" when used herein refers to a detectable compound or composition which can be conjugated directly or indirectly to a molecule or protein, e.g., an antibody. The label may itself be detectable (e.g., radioisotope labels or fluorescent labels) or, in the case of an enzymatic label, may catalyze chemical alteration of a substrate compound or composition which is detectable.

As used herein, "solid phase" means a non-aqueous matrix to which the antibody of the present invention can adhere. Example of solid phases encompassed herein include those formed partially or entirely of glass (e.g. controlled pore glass), polysaccharides (e.g., agarose), polyacrylamides, polystyrene, polyvinyl alcohol, and silicones. In certain embodiments, depending on the context, the solid phase can comprise the well of an assay plate; in others it is a purification column (e.g. an affinity chromatography column).

As used herein, the term "Notch3-mediated disorder" means a condition or disease which is characterized by the overexpression and/or hypersensitivity of the Notch3 receptor. Specifically it would be construed to include conditions associated with cerebral autosomal dominant arteriopathy with subcortical infarcts and leukoencephalopathy (CADASIL), T-cell acute lymphoblastic leukemia, lymphoma, Alagille syndrome, liver disease involving aberrant vasularization; diabetes, ovarian cancer, diseases involving vascular cell fate, rheumatoid arthritis, pancreatic cancer, ovarian cancer, plasma cell neoplasms (such as multiple myeloma, plasma cell leukemia, and extramedullary plasmacytoma), and neuroblastoma (Joutel, et al., *Nature* 383:673 (1996); Joutel, et al., *Semin Cell Dev Biol* 9:619 (1998); Nijjar, et al., *Hepatology* 34:1184 (2001); Screpanti, et al., *Trends Mol Med* 9:30 (2003); Anastasi, et al., *J Immunol* 171:4504 (2003); Lu, et al., *Clin Cancer Res* 10:3291 (2004); Sweeney, et al., *FASEB J* 18:1421 (2004); Yabe, et al., *J Orthop* 10:589 (2005); Buchler, et al., *Ann Surg* 242:791 (2005); Park, et al., *Cancer Res* 66:6312 (2006); Hedvat, et al., *Br J Hematol* 122:728 (2003); van Limpt, et al., *CancerLett* 228:59 (2005)).

Immunogen

Recombinant Notch3 was used in immunizing mice to generate the hybridomas from which the novel antibodies of the present invention were first isolated. Recombinant Notch3 is commercially available from a number of sources (see, e.g., R & D Systems, Minneapolis, Minn., PeproTech, Inc., NJ, and Sanofi Bio-Industries, Inc., Tervose, Pa.). Alternatively, Notch 3 can be expressed from a gene or a cDNA encoding Notch3 by cloning into a plasmid or other expression vector and expressing it in any of a number of expression systems according to methods well known to those of skill in the art. Methods of cloning and expressing nucleic acid sequences are well known (see, for example, U.S. Pat. Nos. 5,821,332 and 5,759,546). Because of the degeneracy of the genetic code, a multitude of nucleotide sequences encoding Notch3 polypeptides may be produced. One may vary the nucleotide sequence by selecting combinations based on possible codon choices. These combinations are made in accordance with the standard triplet genetic code as applied to the nucleotide sequence that codes for naturally occurring Notch3 polypeptide and all such variations are to be considered. Any one of these polypeptides may be used in the immunization of an animal to generate antibodies that bind to Notch3.

The immunogen Notch3 polypeptide may, when beneficial, be expressed as a fusion protein that has the Notch3 polypeptide attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the protein. Fusion segments may include, but are not limited to, immunoglobulin Fc regions, glutathione-S-transferase, β-galactosidase, a poly-histidine segment capable of binding to a divalent metal ion, and maltose binding protein.

Exemplary polypeptides comprise all or a portion of SEQ ID NO. 1 or variants or fragments thereof.

Antibody Generation

The antibodies of the present invention were generated by administering an immunogen as described above to a host animal, in this case a mouse, to induce the production polyclonal antibodies specific for the antigen. The generation of these antibodies is described in Example I. In the hybridoma model, the host animal is immunized to elicit lymphocytes that produce or are capable of producing antibodies that will specifically bind to the protein used for immunization. Lymphocytes then are fused with myeloma cells using a suitable fusing agent, such as polyethylene glycol, to form a hybridoma cell (Goding, Monoclonal Antibodies: Principles and Practice, Academic Press, pp. 59-103 (1986)).

Generally, in making antibody-producing hybridomas, either peripheral blood lymphocytes ("PBLs") are used if cells of human origin are desired, or spleen cells or lymph node cells are used if non-human mammalian sources are desired. Immortalized cell lines are usually transformed mammalian cells, particularly myeloma cells of rodent, bovine or human origin. Typically, a rat or mouse myeloma cell line is employed. The hybridoma cells may be cultured in a suitable culture medium that preferably contains one or more substances that inhibit the growth or survival of the unfused, immortalized cells.

The culture medium in which hybridoma cells of the present invention were grown was assayed for production of monoclonal antibodies directed against Notch3. The binding specificity of monoclonal antibodies produced by hybridoma cells was determined by immunoprecipitation or by an in vitro binding assay, such as radioimmunoassay (RIA) or enzyme-linked immunoabsorbent assay (ELISA). Such techniques are known in the art and within the skill of the artisan. The binding affinity of the monoclonal antibody to Notch3 can, for example, be determined by a Scatchard analysis (Munson, et al., *Anal Biochem* 107:220 (1980)).

After hybridoma cells were identified that produce antibodies of the desired specificity, affinity, and/or activity, the clones were subcloned by limiting dilution procedures and grown by standard methods (Goding, Monoclonal Antibodies: Principles and Practice, Academic Press, pp. 59-103 (1986)). Suitable culture media for this purpose include, for example, Dulbecco's Modified Eagle's Medium (D-MEM) or RPMI-1640 medium. In addition, the hybridoma cells may be grown in vivo as ascites tumors in an animal.

The monoclonal antibodies secreted by the subclones were suitably separated or isolated from the culture medium by conventional immunoglobulin purification procedures such as, for example, protein A-Sepharose, hydroxylaptite chromatography, gel exclusion chromatography, gel electrophoresis, dialysis, or affinity chromatography.

Identification of Anti-Notch 3 Antibodies

The present invention provides monoclonal antibodies that specifically bind Notch3 and allow the detection and/or diagnosis of Notch-3 related diseases and disorders. The antibodies of the present invention include the antibodies designated 255A-71, 255A-77, and 256A-13 having the sequences of SEQ ID NOs 2-7. Candidate anti-Notch3 antibodies were tested by enzyme linked immunosorbent assay (ELISA), Western immunoblotting, or other immunochemical techniques. Assays performed to characterize the individual antibodies are described in the Examples 3 and 4.

The antibodies may be human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and single-domain antibodies comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments comprising any combination of variable region(s) with a hinge region, CH1, CH2, and CH3 domains.

Vectors and Host Cells

In another aspect, the present invention provides isolated nucleic acid sequences encoding an antibody variant as disclosed herein, vector constructs comprising a nucleotide sequence encoding the antibodies of the present invention, host cells comprising such a vector, and recombinant techniques for the production of the antibody.

For recombinant production of the antibody, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody variant). Standard techniques for cloning and transformation may be used in the preparation of cell lines expressing the antibodies of the present invention.

Vectors

Many vectors are available. The vector components generally include, but are not limited to, one or more of the following: a signal sequence, an origin of replication, one or more marker genes, an enhancer element, a promoter, and a transcription termination sequence. Recombinant expression vectors containing a nucleotide sequence encoding the antibodies of the present invention can be prepared using well known techniques. The expression vector may include a suitable transcriptional or translational regulatory sequence such as those derived from mammalian, microbial, viral, or insect genes. Examples of regulatory sequences include transcriptional promoters, operators, enhancers, mRNA ribosomal binding sites, and/or other appropriate sequences which control transcription and translation initiation and termination. Nucleotide sequences may be "operably linked" when the regulatory sequence functionally relates to the nucleotide sequence for the appropriate polypeptide. Thus, a promoter nucleotide sequence is operably linked to, e.g., the antibody heavy chain sequence if the promoter nucleotide sequence controls the transcription of the appropriate nucleotide sequence.

In addition, sequences encoding appropriate signal peptides that are not naturally associated with antibody heavy and/or light chain sequences can be incorporated into expression vectors. For example, a nucleotide sequence for a signal peptide (secretory leader) may be fused in-frame to the polypeptide sequence so that the antibody is secreted to the periplasmic space or into the medium. A signal peptide that is functional in the intended host cells enhances extracellular secretion of the appropriate antibody. The signal peptide may be cleaved from the polypeptide upon secretion of antibody from the cell. Examples of such secretory signals are well known and include, e.g., those described in U.S. Pat. Nos. 5,698,435; 5,698,417; and 6,204,023.

The vector may be a plasmid vector, a single or double-stranded phage vector, or a single or double-stranded RNA or DNA viral vector. Such vectors may be introduced into cells as polynucleotides by well known techniques for introducing DNA and RNA into cells. The vectors, in the case of phage and viral vectors also may be introduced into cells as packaged or encapsulated virus by well known techniques for infection and transduction. Viral vectors may be replication competent or replication defective. In the latter case, viral propagation generally will occur only in complementing host cells. Cell-free translation systems may also be employed to produce the protein using RNAs derived from the present DNA constructs. Such vectors may include the nucleotide sequence encoding the constant region of the antibody molecule (see, e.g., PCT Publications WO 86/05807 and WO 89/01036; and U.S. Pat. No. 5,122,464) and the variable domain of the antibody may be cloned into such a vector for expression of the entire heavy or light chain.

Host Cells

The antibodies of the present invention can be expressed from any suitable host cell. Examples of host cells useful in the present invention include prokaryotic, yeast, or higher eukaryotic cells and also include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., Baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Prokaryotes useful as host cells in the present invention include gram negative or gram positive organisms such as *E. coli, B. subtilis, Enterobacter, Erwinia, Klebsiella, Proteus, Salmonella, Serratia,* and *Shigella,* as well as *Bacilli, Pseudomonas,* and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the pKK223-3 (Pharmacia Fine Chemicals, Uppsala, Sweden), pGEM1 (Promega Biotec, Madison, Wis., USA), and the pET (Novagen, Madison, Wis., USA) and pRSET (Invitrogen Corporation, Carlsbad, Calif., USA) series of vectors (Studier, *J Mol Biol* 219:37 (1991); Schoepfer, *Gene* 124:83 (1993)). Promoter sequences commonly used for recombinant prokaryotic host cell expression vectors include T7, (Rosenberg, et al., *Gene* 56:125 (1987)), β-lactamase (penicillinase), lactose promoter system (Chang, et al., *Nature* 275:615 (1978); Goeddel, et al., *Nature* 281:544 (1979)), tryptophan (trp) promoter system (Goeddel, et al., *Nucl Acids Res* 8:4057 (1980)), and tac promoter (Sambrook, et al., Molecular Cloning, A Laboratory Manual, 2nd ed., Cold Spring Harbor Laboratory (1990)).

Yeasts or filamentous fungi useful in the present invention include those from the genus *Saccharomyces, Pichia, Actinomycetes, Kluyveromyces, Schizosaccharomyces, Candida, Trichoderma, Neurospora,* and filamentous fungi such as *Neurospora, Penicillium, Tolypocladium,* and *Aspergillus*.

Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman, et al., *J Biol Chem* 255:2073 (1980)) or other glycolytic enzymes (Holland, et al., *Biochem* 17:4900 (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer, et al., *Gene* 107:285 (1991). Other suitable promoters and vectors for yeast and yeast transformation protocols are well known in the art. Yeast transformation protocols are well known. One such protocol is described by Hinnen, et al., *Proc Natl Acad Sci* 75:1929 (1978). The Hinnen protocol selects for Trp$^+$ transformants in a selective medium.

Mammalian or insect host cell culture systems may also be employed to express recombinant antibodies. In principle, any higher eukaryotic cell culture is workable, whether from vertebrate or invertebrate culture. Examples of invertebrate cells include plant and insect cells (Luckow, et al., *Bio/Technology* 6:47 (1988); Miller, et al., Genetics Engineering, Setlow, et al., eds. Vol. 8, pp. 277-9, Plenam Publishing (1986); Mseda, et al., *Nature* 315:592 (1985)). For example, Baculovirus systems may be used for production of heterologous proteins. In an insect system, *Autographa californica* nuclear polyhedrosis virus (AcNPV) may be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter). Other hosts that have been identified include *Aedes, Drosophila melanogaster*, and *Bombyx mori*. A variety of viral strains for transfection are publicly available, e.g., the L-1 variant of AcNPV and the Bm-5 strain of *Bombyx mori* NPV, and such viruses may be used as the virus herein according to the present invention, particularly for transfection of *Spodoptera frugiperda* cells. Moreover, plant cells cultures of cotton, corn, potato, soybean, petunia, tomato, and tobacco and also be utilized as hosts.

Vertebrate cells, and propagation of vertebrate cells, in culture (tissue culture) has become a routine procedure. See Tissue Culture, Kruse, et al., eds., Academic Press (1973). Examples of useful mammalian host cell lines are monkey kidney; human embryonic kidney line; baby hamster kidney cells; Chinese hamster ovary cells/−DHFR (CHO, Urlaub, et al., *Proc Natl Acad Sci USA* 77:4216 (1980)); mouse sertoli cells; human cervical carcinoma cells (HELA); canine kidney cells; human lung cells; human liver cells; mouse mammary tumor; and NS0 cells.

Host cells are transformed with the above-described vectors for antibody production and cultured in conventional nutrient media modified as appropriate for inducing promoters, transcriptional and translational control sequences, selecting transformants, or amplifying the genes encoding the desired sequences. Commonly used promoter sequences and enhancer sequences are derived from polyoma virus, Adenovirus 2, Simian virus 40 (SV40), and human cytomegalovirus (CMV). DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are commercially available.

The host cells used to produce the antibody of this invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing host cells. In addition, any of the media described in Ham, et al., *Meth Enzymol* 58:44 (1979), Barnes, et al., *Anal Biochem* 102:255 (1980), and U.S. Pat. No. 4,767,704; 4,657,866; 4,560,655; 5,122,469; 5,712,163; or 6,048,728 may be used as culture media for the host cells. Any of these media may be supplemented as necessary with hormones and/or other growth factors (such as insulin, transferrin, or epidermal growth factor), salts (such as X-chlorides, where X is sodium, calcium, magnesium; and phosphates), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Polynucleotides Encoding Antibodies

The invention further provides polynucleotides or nucleic acids, e.g., DNA, comprising a nucleotide sequence encoding an antibody of the invention and fragments thereof. Exemplary polynucleotides include those encoding antibody chains comprising one or more of the amino acid sequences described herein. The invention also encompasses polynucleotides that hybridize under stringent or lower stringency hybridization conditions to polynucleotides that encode an antibody of the present invention.

The polynucleotides may be obtained, and the nucleotide sequence of the polynucleotides determined, by any method known in the art. For example, a polynucleotide encoding the antibody may be assembled from chemically synthesized oligonucleotides (e.g., as described in Kutmeier, et al., *Bio/Techniques* 17:242 (1994)), which, briefly, involves the synthesis of overlapping oligonucleotides containing portions of the sequence encoding the antibody, annealing and ligating of those oligonucleotides, and then amplifying the ligated oligonucleotides by PCR.

In a specific embodiment, the amino acid sequence of the heavy and/or light chain variable domains may be inspected to identify the sequences of the CDRs by well known methods, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia, et al., *J Mol Biol* 278: 457 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison, et al., Proc Natl Acad Sci 81:851 (1984); Neuberger, et al., Nature 312:604 (1984); Takeda, et al., Nature 314:452 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423 (1988); Huston, et al., Proc Natl Acad Sci USA 85:5879 (1988); and Ward, et al., Nature 334:544 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra, et al., Science 242:1038 (1988)).

Methods of Producing Anti-Notch3 Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative, or analog thereof, (e.g., a heavy or light chain of an antibody of the invention or a single chain antibody of the invention), requires construction of an expression vector containing a polynucleotide that encodes the antibody or a fragment of the antibody. Once a polynucleotide encoding an antibody molecule has been obtained, the vector for the production of the antibody may be produced by recombinant DNA technology. An expression vector is constructed containing antibody coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody molecules of the invention as described above. Such host-expression systems represent vehicles by which the coding sequences of interest may be produced and subsequently purified, but also represent cells which may, when transformed or transfected with the appropriate nucleotide coding sequences, express an antibody molecule of the invention in situ. Bacterial cells such as E. coli, and eukaryotic cells are commonly used for the expression of a recombinant antibody molecule, especially for the expression of whole recombinant antibody molecule. For example, mammalian cells such as NS0 or CHO, in conjunction with a vector such as the major intermediate early gene promoter element from human cytomegalovirus, are an effective expression system for antibodies (Foecking, et al., Gene 45:101 (1986); Cockett, et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for one to two days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler, et al., Cell 11:223 (1977)), hypoxanthine-guanine phosphoribosyltransferase (Szybalska, et al., Proc Natl Acad Sci USA 48:202 (1992)), and adenine phosphoribosyltransferase (Lowy, et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler, et al., Proc Natl Acad Sci USA 77:357 (1980); O'Hare, et al., Proc Natl Acad Sci USA 78:1527 (1981)); gpt, which confers resistance to mycophenolic acid (Mulligan, et al., Proc Natl Acad Sci USA 78:2072 (1981)); neo, which confers resistance to the aminoglycoside G-418 (Wu, et al., Biotherapy 3:87 (1991)); and hygro, which confers resistance to hygromycin (Santerre, et al., Gene 30:147 (1984)). Methods commonly known in the art of recombinant DNA technology may be routinely applied to select the desired recombinant clone, and such methods are described, for example, in Ausubel, et al., eds., Current Protocols in Molecular Biology, John Wiley & Sons (1993); Kriegler, Gene Transfer and Expression, A Laboratory Manual, Stockton Press (1990); and in Chapters 12 and 13, Dracopoli, et al., eds, Current Protocols in Human Genetics, John Wiley & Sons (1994); Colberre-Garapin, et al., J Mol Biol 150:1 (1981), which are incorporated by reference herein in their entireties.

The expression levels of an antibody molecule can be increased by vector amplification (for a review, see Bebbington, et al., "The use of vectors based on gene amplification for the expression of cloned genes in mammalian cells," DNA Cloning, Vol. 3. Academic Press (1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse, et al., *Mol Cell Biol* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, it may be preferable to place the light chain before the heavy chain to avoid an excess of free heavy chain (Proudfoot, *Nature* 322:52 (1986); Kohler, *Proc Natl Acad Sci USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., PCT publication WO 93/21232; EP 439,095; Naramura, et al., *Immunol Lett* 39:91 (1994); U.S. Pat. No. 5,474,981; Gillies, et al., *Proc Natl Acad Sci USA* 89:1428 (1992); Fell, et al., *J Immunol* 146:2446 (1991), which are incorporated by reference in their entireties.

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz, et al., *Proc Natl Acad Sci USA* 86:821 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson, et al., *Cell* 37:767 (1984)) and the "flag" tag.

Antibody Purification

When using recombinant techniques, the antibodies of the present invention can be produced intracellularly, in the periplasmic space, or directly secreted into the medium. If the antibodies are produced intracellularly, as a first step, the particulate debris, either host cells or lysed fragments, may be removed, for example, by centrifugation or ultrafiltration. Carter, et al., *Bio/Technology* 10:163 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. When the antibodies are secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody variant. Protein A can be used to purify antibodies that are based on human IgG1, IgG2 or IgG4 heavy chains (Lindmark, et al., *J Immunol Meth* 62:1 (1983)). Protein G is recommended for all mouse isotypes and for human IgG3 (Guss, et al., *EMBO J* 5:1567 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Diagnostic Uses for Anti-Notch3 Antibodies

The antibodies of the invention include derivatives that are modified, i.e., by the covalent attachment of any type of molecule to the antibody, such that covalent attachment does not interfere with binding to Notch3. For example, but not by way of limitation, the antibody derivatives include antibodies that have been modified, e.g., by biotinylation, HRP, or any other detectable moiety.

Antibodies of the present invention may be used, for example, but not limited to, to purify or detect Notch3, including both in vitro and in vivo diagnostic methods. For example, the antibodies have use in immunoassays for qualitatively and quantitatively measuring levels of Notch3 in biological samples. See, e.g., Harlow, et al., Antibodies: A Laboratory Manual, Cold Spring Harbor Laboratory Press, 2nd ed. (1988), which is incorporated by reference herein in its entirety.

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays.

The present invention further encompasses antibodies or fragments thereof conjugated to a diagnostic agent. The antibodies can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. Examples of fluorescent labels include rare earth chelates (europium chelates) and fluorescein and its derivatives, rhodamine and its derivatives, dansyl, Lissamine, phycoerythrin and Texas Red. The fluorescent labels can be conjugated to the antibody using the techniques disclosed in *Current Protocols in Immunology*, Volumes 1 and 2, Coligen, et al., Ed. Wiley-Interscience, New York (1991), for example. Fluorescence can be quantified using a fluorimeter. Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate, which may b equantified using a fluorimeter. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, beta.-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan, et al., "Methods for the Preparation of Enzyme-Antibody Conjugates for Use in Enzyme Immunoassay," in Methods in Enzymology, Langone, et al., eds. pp. 147-66, Academic Press (1981). See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digloxin) and one of the different types of labels mentioned above is conjugated with an anti-hapten antibody (e.g., anti-digloxin antibody). Thus, indirect conjugation of the label with the antibody variant can be achieved.

In another embodiment of the invention, the antibody need not be labeled, and the presence thereof can be detected using a labeled antibody which binds to the antibody.

The antibodies of the present invention may be employed in any known assay method, such as competitive binding assays, direct and indirect sandwich assays, and immunoprecipitation assays. See Zola, Monoclonal Antibodies: A Manual of Techniques, pp. 147-158, CRC Press (1987).

Competitive binding assays rely on the ability of a labeled standard to compete with the test sample for binding with a limited amount of antibody variant. The amount of target in the test sample is inversely proportional to the amount of standard that becomes bound to the antibodies. To facilitate determining the amount of standard that becomes bound, the antibodies generally are insolubilized before or after the competition. As a result, the standard and test sample that are bound to the antibodies may conveniently be separated from the standard and test sample which remain unbound.

Sandwich assays involve the use of two antibodies, each capable of binding to a different immunogenic portion, or epitope, or the protein to be detected. In a sandwich assay, the test sample to be analyzed is bound by a first antibody which is immobilized on a solid support, and thereafter a second antibody binds to the test sample, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Antibodies may be attached to solid supports, which are particularly useful for detection of Notch 3 in a sample. These antibodies are also useful for affinity purification agents, in immunoassays or purification of the target antigen. Such solid supports include, but are not limited to, glass, cellulose, polyacrylamide, nylon, polystyrene, polyvinyl chloride or polypropylene. These may take the form of a microtiter plate, a slide, a bead, a tube, resins such as SEPHADEX™ resin, filter paper or any other support useful in the attachment of an antibody for such purposes. In this process, the antibodies are immobilized on a solid support using methods well known in the art. The immobilized antibodies are contacted with a sample containing the target to be detected or purified, and thereafter the support is washed with a suitable solvent that will remove substantially all the material in the sample except the target, which is bound to the immobilized antibodies. The antibodies can then be detected by typical means such as calorimetric assays, chemiluminscent assays, or by radioactive labeling. If the antibody is being used for purification, the support may be washed with another suitable solvent, such as glycine buffer, that will release the target from the antibodies.

Labeled antibodies, and derivatives and analogs thereof, which specifically bind to Notch3 can be used for diagnostic purposes to detect, diagnose, or monitor diseases, disorders, and/or conditions associated with the aberrant expression and/or activity of Notch3. The invention provides for the detection of aberrant expression of Notch3, comprising (a) assaying the expression of Notch3 in cells or body fluid of an individual using one or more antibodies of the present invention specific to Notch3 and (b) comparing the level of gene expression with a standard gene expression level, whereby an increase or decrease in the assayed Notch3 expression level compared to the standard expression level is indicative of aberrant expression.

Antibodies may be used for detecting the presence and/or levels of Notch3 in a sample, e.g., a bodily fluid or tissue sample. The detecting method may comprise contacting the sample with a Notch3 antibody and determining the amount of antibody that is bound to the sample. For immunohistochemistry, the sample may be fresh or frozen or may be embedded in paraffin and fixed with a preservative such as formalin, for example.

The invention provides a diagnostic assay for diagnosing a disorder, comprising (a) assaying the expression of Notch3 in cells or body fluid of an individual using one or more antibodies of the present invention and (b) comparing the level of Notch3 protein expression with a standard protein expression level, whereby an increase or decrease in the assayed expression level compared to the standard expression level is indicative of a particular disorder.

Antibodies of the invention can be used to assay protein levels in a biological sample using classical immunohistological methods known to those of skill in the art (e.g., see Jalkanen, et al., *J Cell Biol* 101:976 (1985); Jalkanen, et al., *J Cell Biol* 105:3087 (1987)). The antibodies may also be used for in vivo diagnostic assays. Other antibody-based methods useful for detecting protein expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{121}$I), carbon ($^{14}$C), sulfur ($^{35}$S), tritium ($^{3}$H), indium ($^{112}$In, $^{111}$In), and technetium ($^{99}$Tc); luminescent labels, such as luminol; and fluorescent labels, such as fluorescein, rhodamine, and biotin. Radioisotope-bound isotopes may be localized using immunoscintiography. The antibody can be labeled with the radioisotope suing the techniques described in *Current Protocols in Immunology*, Volumes 1 and 2, Coligen, et al., Ed. Wiley-Interscience, New York (1991) for example and radioactivity can be measured using scintillation counting.

In one embodiment, a method of detecting Notch3 in a biological sample (e.g., tissue, blood, sera) or a prepared biological sample can comprise the step of contacting an antibody of this invention with the sample and observing the anti-Notch3 antibody bound to the Notch3 in the sample or determining the amount of the anti-Notch3 antibody bound to Notch3 in the sample.

In another embodiment, a method of detecting Notch3 in a subject comprises the step of administering an antibody of this invention to the subject and observing the anti-Notch3 antibody bound to the Notch3 in the subject or determining the amount of the anti-Notch3 antibody bound to Notch3 in the subject (e.g., human, mouse, rabbit, rat, etc.).

One aspect of the invention is the detection and diagnosis of a disease or disorder associated with aberrant expression of Notch3 in an animal, preferably a mammal and most preferably a human. In one embodiment, diagnosis comprises: a) administering (for example, parenterally, subcutaneously, or intraperitoneally) to a subject an effective amount of a labeled molecule which specifically binds to Notch3; b) waiting for a time interval following the administration permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of Notch3. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo imaging is described in Burchiel, et al., "Immunopharmacokinetics of Radiolabeled Antibodies and Their Fragments." Chapter 13 in Tumor Imaging: The Radiochemical Detection of Cancer, Burchiel, et al., eds., Masson Publishing (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours, 6 to 24 hours, or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

In another aspect, the present invention provides a method for diagnosing the predisposition of a patient to develop diseases caused by the unregulated expression of cytokines. Increased amounts of Notch3 in certain patient cells, tissues, or body fluids may indicate that the patient is predisposed to certain diseases. In one embodiment, the method comprises collecting a cell, tissue, or body fluid sample a subject known to have low or normal levels of Notch3, analyzing the tissue or body fluid for the presence of Notch3 in the tissue, and predicting the predisposition of the patient to certain diseases based upon the level of expression of Notch3 in the tissue or body fluid. In another embodiment, the method comprises collecting a cell, tissue, or body fluid sample known to contain a defined level of Notch3 from a patient, analyzing the tissue or body fluid for the amount of Notch3, and predicting the predisposition of the patient to certain diseases based upon the change in the amount of Notch3 compared to a defined or tested level established for normal cell, tissue, or bodily fluid. The defined level of Notch3 may be a known amount based upon literature values or may be determined in advance by measuring the amount in normal cell, tissue, or body fluids. Specifically, determination of Notch3 levels in certain tissues or body fluids permits specific and early, preferably before disease occurs, detection of diseases in the patient. Diseases that can be diagnosed using the present method include, but are not limited to, the diseases described herein. In the preferred embodiment, the tissue or body fluid is peripheral blood, peripheral blood leukocytes, biopsy tissues such as lung or skin biopsies, and tissue.

The antibody of the present invention can be provided in a kit, i.e., packaged combination of reagents in predetermined amounts with instructions for performing the diagnostic assay. Where the antibody is labeled with an enzyme, the kit may include substrates and cofactors required by the enzyme (e.g., a substrate precursor which provides the detectable chromophore or fluorophore). In addition, other additives may be included, such as stabilizers, buffers (e.g., a block buffer or lysis buffer), and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

EXAMPLES

The following examples are offered by way of illustration and not by way of limitation.

Example 1

Generation of Immunogen: Notch3 Extracellular Domain-FC Fusion Protein

Notch3 protein sequence was analyzed using an internet-based research software and service (Motif Search). The extracellular moiety of Notch3 consists of 34 epithelial growth factor (EGF) repeats, three LIN12 signature motifs, and a heterodimerization domain. The cDNAs coding for the EGF repeat region (amino acid 43-1377) and LIN12/dimerization (LD) domain (amino acid 1378-1640) of Notch3 were synthesized by PCR amplification from human liver and pancreatic RNAs (Ambion, Inc. Austin, Tex.), respectively, followed by a first strand cDNA synthesis using Invitrogen's Superscriptase III cDNA synthesis kit and protocol (Invitrogen, Carlsbad, Calif.). The PCR-synthesized Notch3-EGF repeat DNA fragment (~4 kb) and Notch3-LD DNA fragment (~0.8 kb) were cloned into Tanox's internally generated expression vectors, His-γ1Fc/pSec and His-γ1Fc/pCD3.1, which resulted two sets of expression plasmids, one expressing Notch3-EGF/Fc fusion protein and the other expressing Notch3-LD/Fc fusion protein. In both of the fusion proteins, a signal peptide was linked to the N-terminus, and a human γ1Fc sequence was fused to C-terminus of Notch3-EGF or Notch3-LD.

Expression of Notch3-EGF/Fc and Notch3-LD/Fc fusion proteins was verified by transient transfection of the Notch3 expression plasmids into 293T (American Type Culture Collections (ATCC Number CRL-11268), Manassas, Va.) and Flip-in CHO cells (Invitrogen, Carlsbad, Calif.), respectively. Prior to transfection, cells were cultured in DMEM (Invitrogen, Carlsbad, Calif.) growth medium containing 10% fetal calf serum (FCS), 2 mM of glutamine, and 1× essential amino acid solution (Invitrogen, Carlsbad, Calif.), followed by seeding $3\text{-}5\times10^5$ cells per well in 6-well plate and growing for 24 hours. Three micrograms each of the Notch3 fusion protein expression plasmids were transfected into each well using Invitrogen's Lipofectamine 2000 transfection system (Invitrogen, Carlsbad, Calif.) following manufacturer's protocol. After transfection, the cells were cultured in growth medium for 3-4 hours, then switched to DMEM medium containing 2% FCS and cultured for 60-66 hours before drawing conditioned medium for secreted protein analysis.

For stable cell line generation, each of the fusion protein containing plasmids, Notch3-EGF/Fc (His-Fcγ/pSec backbone vector) and Notch3-LD/Fc (within His-Fcγ/pSec), were cotransfected with pOG-44 (Invitrogen, Carlsbad, Calif.) into Flip-in CHO cells. After transfection, the cells were cultured in DMEM growth medium overnight, followed by a transfer into growth medium containing 800 µg/ml hygromycin and then cultured for at least two weeks until the cells not carrying Notch3 expression plasmid DNA were eliminated by antibiotics. Cells exhibiting hygromycin resistance were established as stable cells lines for further testing.

Transient and stable cell lines were subjected to Western blot analysis to verify the expression and secretion of Notch3-EGF/Fc or Notch3-LD/Fc fusion protein. Transfected cells were harvested from culture dishes, washed once with phosphate buffered saline (PBS), resuspended in deionized water, followed by adding an equal volume of 2× protein sample loading buffer (BioRad, Hercules, Calif.), heating at 100° C. for 10 minutes, and loading on an SDS-PAGE gel. In addition, secreted protein from the medium was also analyzed by mixing an equal volume of conditioned medium with 2× protein sample loading buffer, heating at 100° C. for 10 minutes, and loading on an SDS-PAGE gel. The samples were separated by electrophoresis in a 4-15% gradient SDS-PAGE (BioRad, Hercules, Calif.). The proteins were transferred from the gel to a PVDF membrane (BioRad, Hercules, Calif.). Non-specific binding sites were blocked using 5% non-fat dry milk in PBST (PBS with 0.05% tween-20) for at least one hour. The presence of Notch3-EGF/Fc and/or Notch3-LD/Fc fusion proteins was detected by incubation with γFc-specific, HRP-conjugated antibody (Sigma, St Louis, Mo.) in blocking buffer for one hour at room temperature. The membrane was washed three times in PBST and developed with Supersignal Chemiluminescent Substrate (Pierce, Rockford, Ill.) according to the manufacturer's protocol.

After verifying that the fusion proteins were expressed and exhibited the correct banding pattern on Western blots, Notch3/Fc fusion protein was generated for purification. The stable cell line generated as described above was cultured in DMEM with 2% FCS for up to 5 days. One liter of conditioned medium was collected and subjected to protein-A affinity binding. The column was washed with PBS and the bound proteins were eluted in 50 mM citrate buffer (pH2.8). The pH was then brought to neutral by adding 1 M Tris-HCl buffer (pH8). The purified protein was analyzed by protein gel analysis using 4-15% gradient SDS-PAGE. The protein concentration was assayed using Coomassie blue reagent following the manufacturer's protocol (Pierce, Rockford, Ill.). Through this procedure, milligram quantities of Notch3-EGF/Fc and Notch3-LD/Fc protein were purified for immunization and ELISA binding assays.

Example 2

Generation of Anti-Notch3 MABS

Male A/J mice (Harlan, Houston, Tex.), 8-12 week old, were injected subcutaneously with 25 μg of Notch3-EGF/Fc or Notch3-LD/Fc in complete Freund's adjuvant (Difco Laboratories, Detroit, Mich.) in 200 μl of PBS. At two-week intervals, the mice were twice injected subcutaneously with 25 μg of Notch3-EGF/Fc or Notch3-LD/Fc in incomplete Freund's adjuvant, respectively. Two weeks after the injections and three days prior to sacrifice, the mice were again injected intraperitoneally with 25 μg of the same antigen in PBS. For each fusion, single cell suspensions were prepared from spleen of an immunized mouse and used for fusion with Sp2/0 myeloma cells; $5 \times 10^8$ of Sp2/0 and $5 \times 10^8$ of spleen cells were fused in a medium containing 50% polyethylene glycol (M.W. 1450) (Kodak, Rochester, N.Y.) and 5% dimethylsulfoxide (Sigma, St. Louis, Mo.). The cells were then adjusted to a concentration of $1.5 \times 10^8$ spleen cells per 200 μl of the suspension in Iscove medium (Invitrogen, Carlsbad, Calif.), supplemented with 10% fetal bovine serum, 100 units/ml of penicillin, 100 μg/ml of streptomycin, 0.1 μM hypoxanthine, 0.4 μM aminopterin, and 16 μM thymidine. Two hundred microliters of the cell suspension were added to each well of about sixty 96-well plates. After about ten days, culture supernatants were withdrawn for screening their antibody-binding activity using ELISA.

The 96-well flat bottom Immulon II microtest plates (Dynatech, Laboratories, Chantilly, Va.) were coated using 100 μl of Notch3-EGF/Fc or Notch3-LD/Fc (0.1 μg/ml) in phosphate buffered saline (PBS) containing 1× Phenol Red and 3-4 drops pHix/liter (Pierce, Rockford, Ill.) and incubated overnight at room temperature. After the coating solution was removed by flicking of the plate, 200 μl of blocking buffer containing 2% BSA in PBST (1×PBS with 0.05% Tween-20 and 0.1% merthiolate) was added to each well for one hour to block non-specific binding. The wells were then washed with PBST (PBS with 0.05% Tween-20). Fifty microliters of culture supernatant from each fusion well was collected and mixed with 50 μl of blocking buffer and then added to the individual wells of the microtiter plates. After one hour of incubation, the wells were washed with PBST. The bound murine antibodies were then detected by reaction with horseradish peroxidase (HRP)-conjugated, Fc-specific goat anti-mouse IgG (Jackson ImmunoResearch Laboratories, West Grove, Pa.). HRP substrate solution containing 0.1% 3,3,5,5-tetramethyl benzidine and 0.0003% hydrogen peroxide (Sigma, St. Louis, Mo.) was added to the wells for color development for 30 minutes. The reaction was terminated by the addition of 50 ml of 2 M $H_2SO_4$, per well. The OD at 450 nm was read with an ELISA plate reader (Molecular Devices, Sunnyvale, Calif.). The ELISA using supernatant from the three hybridoma clones producing mAbs 255A-71, 255A-77, and 256A-13 showed strong binding activity to the purified Notch3/FC fusion protein to which it was generated (Table 1).

TABLE 1

ELISA OD readings of anti-Notch3 Mabs using hybridoma supernatant

| Hybridoma supernatant | ELISA coating protein | | | | | |
|---|---|---|---|---|---|---|
| | Notch3-EGF/Fc | | Notch3-EGF/Fc | | Notch3-LD/Fc | |
| | Control | 255A-71 | Control | 255A-77 | Control | 256A-13 |
| Mean | 0.010 | 2.225 | 0.019 | 1.717 | 0.019 | 2.828 |
| S.D. | 0.003 | 0.064 | 0.003 | 0.059 | 0.002 | 0.047 |

Note:
Controls were hybridoma clones without specific binding activity to Notch3.

The positive hybridoma clones from this primary ELISA screening were further isolated by single colony-picking and a second ELISA assay as described above was done to verify specific binding to the chosen immunogen. The confirmed hybridoma clones were expanded in larger scale cultures. The monoclonal antibodies (mAbs) were purified from the medium of these large scale cultures using a protein A affinity column. The anti-Notch3 mAbs were then characterized using cell-based binding assays, microscopy, Western blot, and FACS analysis.

Example 3

Cell-Based Binding Assays for Anti-Notch3 MABS

The cell-based binding assays used to characterize the anti-Notch 3 mAbs required cloning a full-length of human Notch3 open reading frame into a vector, in this case pcDNA3.1/Hygro (Invitrogen, Carlsbad, Calif.). The Notch3-coding region was synthesized by RT-PCR using human liver tumor RNA (Ambion, Inc., Austin, Tex.) as a template. The final plasmid construct, Notch3/Hygro, expressed a full-length Notch3 protein as depicted in FIG. 1. A stable cell line expressing Notch3 was generated by transfecting the plasmid construct into 293T cells using a Lipofectamine 2000 kit following the same procedure as described in Example 1. Well-isolated single colonies were picked up and grown in separate wells until enough clonal cells were amplified. Stable 293T clones that were resistant to hygromycin and expressed high levels of Notch3 protein were identified by Western blot analysis and by fluorescent electromicroscopy using polyclonal anti-Notch3 antibodies (R&D Systems, Minneapolis, Minn.).

A Notch3 expression plasmid comprising only the Notch LIN12/dimerization (LD) domain and the transmembrane (TM) domain was also constructed by PCR and subcloning into pcDNA3.1 (Invitrogen, Carlsbad, Calif.). This plasmid construct also contains a V5 tag at its C-terminus and was termed Notch3-LDTM/V5. A stable cell line expressing this plasmid was generated according to the procedure described in Example 1.

Human Sup-T1 cell line (ATCC CRL-1942), which naturally expresses Notch3, was used as a control in the FACS analysis. This cell line's Notch 3 expression was confirmed by Western blot analysis. Sup-T1 cells were cultured in RPMI1640 media containing 10% fetal calf serum, 2 mM of glutamine and 1× essential amino acid solution (Invitrogen, Carlsbad, Calif.) and Western blot was performed as described in Example 1.

Cell-based antibody-binding was assessed using FMAT™ 8100 HTS System (Applied Biosystems, Foster City, Calif.) and protocol provided by the manufacturer with some modification. Cell lines expressing Notch3 were seeded in 96-well plates at a density of 30,000-50,000 cells per well. After 20-24 hours, anti-Notch3 mAbs and 1×PBS reaction buffer were added to the wells and incubated for one hour at 37° C. Cy-5-conjugated anti-mouse IgG antibody was added to the wells after removal of primary antibodies. The fluorescent intensity of bound antibody was measured by FMAT™ 8100 HTS System.

Cell-based antibody-binding was also assessed by fluorescence-activated cell sorter (FACS). Cells were first incubated with anti-Notch3 mAbs in 1×PBS. After three washes, the cells were incubated with fluorescent molecule-conjugated secondary antibody. The cells were resuspended, fixed in 1×PBS with 0.1% paraformaldehyde, and analyzed by FACS machine (BD Sciences, Palo Alto, Calif.). Cell-based FMAT (fluorescence macro-confocal high-throughput screening) assay and FACS analysis confirmed that all three mAbs 255A-71, 255A-77, and 256A-13 indeed bind to the Notch3 receptor expressed either from recombinant plasmid constructs or as native protein in cultured cells (Table 2 and Table 3).

TABLE 2

Summary of anti-Notch3 mAbs binding activity in cell-based FMAT assay

|  | 255A-71 | 255A-77 | 256-13 |
| --- | --- | --- | --- |
| Notch3 (full-length) | good | good | weak |
| Notch3-LDTM | no binding | no binding | good |

TABLE 3

Mean fluorescence intensity of FACS analysis using Notch3/Hygromycin-transiently transfected 293T and Sup-T1 cells

|  | Control IgG1 | 255A-71 | 255A-77 | 256A-13 |
| --- | --- | --- | --- | --- |
| Notch3/Hyg | 24.16 | 124.06 | 242.3 | 32.2 |
| Sup-T1 | 24.51 | 58.16 | 70.53 | 55.44 |

Two of the anti-Notch3 mAbs, 255A-71 and 255A-77, generated from Notch3-EGF/Fc specifically bind to the Notch3-EGF repeat region. The third mAb, 256A-13, generated from Notch3-LD/Fc specifically binds to Notch3-LD domain (Table 2 and 4).

Transiently transfected 293T cells with Notch3/Hygro plasmid were also stained with immunofluorescence as described above and observed by fluorescent microscopy.

Example 4

Western Blot Analysis of Anti-Notch3 MABS Binding Activity

Western blot was performed to assess anti-Notch3 mAbs binding activity to Notch3 under denaturing condition. For this purpose, purified Notch3-EGF/Fc and Notch3-LD/Fc fusion proteins were combined with protein loading buffer (BioRad, Hercules, Calif.). Protein samples were also prepared from the transiently or stably transfected cells described in Example 1, which were harvested from culture dishes, washed once with phosphate buffered saline (PBS), resuspended in deionized water, and heated at 100° C. for 10 minutes after adding equal volume of 2× protein sample loading buffer (BioRad, Hercules, Calif.). All samples were separated by electrophoresis in a 4-15% gradient SDS-PAGE (BioRad, Hercules, Calif.). The proteins were transferred from gel to PVDF membrane (BioRad, Hercules, Calif.) and anti-Notch3 mAbs were applied to the Western blot membrane as the primary detection antibody. An HRP-conjugated secondary antibody was used for detection and the signal generated using a Supersignal Chemiluminescent Substrate (Pierce, Rockford, Ill.) as described above.

Western blot analysis under denatured condition showed that mAb 256A-13 has strong binding activity for denatured Notch3 protein. mAb 255A-71 also binds to denatured Notch3 protein with lower affinity, while mAb 255A-77 does not bind to the denatured protein (Table 4).

TABLE 4

Summary of Western blot band intensity using anti-Notch3 Mabs

|  | 255A-71 | 255A-77 | 256-13 |
| --- | --- | --- | --- |
| Notch3-EGF/Fc | weak | no binding | no binding |
| Notch3-LD/Fc | no binding | no binding | strong |
| Notch3 (full-length) | weak | no binding | strong |

Example 5

Sequencing of Anti-Notch3 MABS

Before sequencing the anti-Notch3 mAbs, the antibody IgG subtype was determined using Isostrip Mouse Monoclonal Antibody kit (Roche Diagnostics, Indianapolis, Ind.). The results showed that all three mAbs, 255A-71, 255A-77 and 256A-13, comprised of an $IgG_1$ heavy chain and kappa light chain.

The variable region sequences of heavy chain and light chain were decoded through RT-PCR and cDNA cloning. Total RNAs from each hybridoma clone of mAbs 255A-71, 255A-77 and 256A-13 were isolated using RNeasy Mini kit and following manufacturer's protocol (Qiagen Sciences, Valencia, Calif.). First strand cDNA was synthesized using the RNA template and Superscriptase III kit (Invitrogen, Carlsbad, Calif.). The variable region of light chain and heavy chain cDNAs were PCR-amplified (High Fidelity PCR System, Roche) from first strand cDNA using degenerative forward primers covering the 5'-end of mouse kappa chain coding region and a reverse primer matching the constant region at juncture to the 3'-end of variable region, or using degenerative forward primers covering the 5'-end of mouse heavy chain coding region and a constant region reverse primer in mouse heavy chain. The PCR product was cloned into pCRII-TOPO following manufacturer's protocol (Invitrogen, Carlsbad, Calif.), and sequenced by Lone Star Lab (Houston, Tex.). The nucleotide sequences were analyzed utilizing computer software program DNAStar (DNASTAR, Inc., Madison, Wis.). Each of the anti-Notch3 mAb sequences was determined by sequences from multiple PCR clones derived from same hybridoma clone.

The variable heavy chain region of MAb 255A-71 contains 123 amino acid residues and the light chain variable region contains 116 amino acid residues (FIGS. 2A and 2B). The variable heavy chain region of mAb 255A-77 contains 120 amino acid residues and the light chain variable region contains 123 amino acid residues (FIGS. 3A and 3B). The variable heavy chain region of mAb 256A-13 contains 121 amino acid residues and the light chain variable region contains 102 amino acid residues (FIGS. 4A and 4B).

Example 6

Detection Using Anti-Notch3 MABS

A. Biopsy Sample Fixation and Slide Preparation

Tumor or tissue samples are removed from a subject suspected of having a Notch 3 related disorder or disease. The sample is placed in cold PBS. The samples are washed with PBS to remove any blood or other substances, and then cut to the proper size, generally thinner than 3 mm for better fixation. The sample is placed in a fixative, such as 4% paraformaldehyde or 10% buffered formalin, and allowed to fix at 4° C. for 10-15 minutes or one hour in a rotating plate. The samples are changed to fresh fixative and incubated at 4° C. for overnight.

The fixed samples are washed once with PBS for 1 minute, followed by three 20-minute-washes with PBS. The samples are then serially dehydrated as follows: 30% ethanol [volume/volume in $ddH_2O$ (distilled deionized water)] for 1 hour, 50% ethanol for 1 hour, 70% ethanol overnight or over a weekend, 95% ethanol for 3 hour or overnight for twice, and finally two 1-hour dehydration in 100% ethanol. The samples may be stored at −20° C. For slide preparation, the samples are incubated three times in 100% ethanol at room temperature, each for one hour. Then, the samples are incubated two times in xylene each for 30-40 minutes, and three times in paraffin each for 40 minutes. Finally, the samples are embedded for cutting and slide-amounting. The slides may be stored at 4° C.

B. Immunohistochemical Staining

To prepare slides for immunostaining, slide tissue sections are deparaffinized twice in Xylene each for 20 minutes, and rehydrated by soaking in 100%, 95% ethanol and ddH2O each for 2 minutes. The slides may be kept in ddH2O prior to immunostaining. Alternatively, antigen retrieval is performed to enhance immunostaining. A glass beaker filled with 1000 ml ddH2O is heated on a hotplate to 95-99° C. or 102-104° C. The slides from above are soaked in antigen-retrieval buffer, 1X Bulls Eye solution (BioCare) in a slide container jar, which is immediately placed in the hot water beaker, heated for 20 minutes and subsequently washed with ddH2O 2-3 times.

For immunostaining, the slides are washed twice in PBS each for 3 minutes, and incubated in PBS containing 3% hydrogen peroxidase for 15 minutes to block the endogenous peroxidase. The slides are then washed three times in PBST (PBS with 0.1% Tween®-20) for 2 minutes per wash. Non-specific proteins are blocked by incubating with 10% normal serum in 0.5% PBST (0.5% Tween®-20 in PBS) for 30-60 minutes at room temperature. The slides are incubated with anti-Notch3 antibody (the first antibody) in 5% normal goat serum in 0.1% PBST overnight at 4° C., followed by six washes with PBST each for 5 minutes. Then, the slides are incubated with 1:200 biotinylated 2nd antibody (detection antibody) for 1 hour at room temperature and are washed six times with PBST each for 5 minutes. Slides are incubated in 1/50 ABC/PBS buffer for 45-60 minutes, followed by four 5-minute washes in PBST and two 5-minute-washes in 0.1M Tris, pH 7.5/0.3M NaCl. To develop the color, DAB solution (one DAB tablet in 5 ml ddH2O, Sigma reagent and protocol) is added to the slides for 2-10 minutes and the slides are washed several times with ddH2O. The slides are counterstained with Hematoxylin for 1 minute, washed, dehydrated, and mounted with mounting medium and cover slide. The Notch3 positive staining may be observed by microscopy, and quantified by manual or automatic microscopic instrument.

Example 7

Examining Soluble Notch3 in Serum by ELISA

Blood samples are collected from a subject and stored in tubes at 4° C. Serum is taken from top layer after precipitation of blood cells and used to examine soluble Notch3 by ELISA described as follows. The 96-well ELISA plate is coated with capture antibody, i.e., anti-Notch3 antibody, which is diluted to 1-4 µg/ml in PBS and distributed at 50 µl per well. The plate is sealed and incubated overnight at 4° C. After bringing the plate to room temperature, the capture antibody solution is removed and non-specific binding is blocked by adding 200 µl of blocking buffer containing 10% fetal bovine serum (FBS), 10% newborn calf serum (NBCS), or 1% BSA (immunoassay grade) in PBS, and incubated at room temperature for 1-2 hours. The plate is then washed at least three times with PBST (0.5% Tween®-20 in PBS).

The serum samples are serially diluted in blocking buffer with 0.5% TWEEN®-20, and 100 µl of the diluted samples are added to each well. The plate is sealed and incubated for 2-4 hours at room temperature or overnight at 4° C. The plates are washed with PBST. For detection, a secondary antibody that recognizes the different epitope of Notch 3 than the capture antibody is used. This second antibody is labeled with, for example, horseradish peroxidase (HRP) and added to each well at a concentration of about 0.1-1 ug/ml. The plate is sealed and incubated at room temperature for 30 minutes. The wells are washed at least 5 times with PBST. Color development solution is prepared by dissolving 150 mg 2,2'-azino-bis-(3-ethylbenzthiazoline-6-sulfonic acid (Sigma) in 500 ml of 0.1 M citric acid, pH 4.35 (Fisher), and 100 µl is dispensed into each well. The plate is incubated at room temperature for 5-80 minutes for color development. The optical density (OD) is read with a microplate reader setting at 405.

Example 8

Detecting Circulating Cancer Cells (CTC) by Anti-Notch3 Antibody Staining

CTCs are indicative of cancer metastasis, which occur when cells shed from the invasive primary tumor enter the circulation and begin to grow in distant locations in the body. Using targeted antibodies against specific markers on the tumor cells, CTCs are detected from the peripheral blood of patients, which has been linked to disease progression.

A. Enrichment of Circulating Tumor Cells from the Blood by Gradient Centrifugation Blood samples are drawn from a subject and stored in 4° C. for processing within 24 hours using, for example, Onco-Quick density gradient system (Greiner Bio-One GmbH, Frickenhausen, Germany). OncoQuick is a separation device composed of a centrifugation tube with a liquid density separation medium and a porous barrier membrane optimized for the enrichment of circulating tumor cells from blood. The blood is layered on top of the gradient, and centrifuged for 20 minutes with 1,600×g at 4° C. The complete supernatant above the porous barrier is transferred into a new tube pre-treated with the washing buffer delivered with the OncoQuick device and cells are washed twice with 50 ml of washing buffer by centrifugation at 200×g at 4° C. for 5 minutes. After the second washing step, the cells are resuspended in 1 ml washing buffer, counted in a Neubauer chamber, and centrifuged at 110×g for 3 minutes using a cytocentrifuge (Hettich model 16 A, Tuttlingen, Germany) on adhesive slides (Superfrost Plus, Menzel Glassware, Braunschweig, Germany) at a concentration of $5 \times 10^5$ cells per area of 240 mm² or an equal cellular density of a smaller area when less cells were retrieved from the gradient. Cytospin slides were air-dried overnight and stored at −80° C. until staining.

B. Immunocytochemical Staining for the Identification of Circulating Tumor Cells in the Blood Slides are fixed according to the manufacturer's instructions with Solution B of the Epimet Kit (Micromet, Martinsried, Germany) containing formaldehyde. After blocking with a serum-free blocking reagent (Dako) for 20 minutes, the slides are incubated with fluorochrome (such as Cy3) conjugated anti-Notch3 antibody and simultaneously counterstained with anti-CD45 antibody labeled with FITC at a dilution of 1/50 to 1/200 for 45 minutes. Finally, the slides are incubated for 1 minute with 4',6-diamidino-2-phenylindole (Sigma, Deisenhofen, Germany), mounted with 0.9% (w/v) NaCl and covered with coverslips. Cells are classified as circulating tumor cells when staining was positive for Notch3, negative for CD45, and when morphologic criteria were fulfilled.

Example 9

Detecting Disseminated Tumor Cells in Bone Marrow

Bone marrow is aspirated directly after surgery under general anesthesia from both iliac crests, and screened for the presence of Notch3-positive cells. In brief, $2 \times 10^6$ mononuclear cells of each bone marrow specimen are analyzed. The anti-Notch3 antibody is used at a concentration of 1-5 μg/ml to detect tumor cells in the cytospin preparation method described above. A negative staining control is obtained by using an unrelated mouse-myeloma IgG1 antibody (MOPC 21, Sigma) at 1-5 μg/ml. The Sup T1 T-cell line described above in Example 3 may serve as a positive control for Notch3 immunostaining in each staining batch. The specific reaction of the primary antibody is developed with the alkaline phosphatase anti-alkaline phosphatase technique (Dako), combined with the fuchsin staining, to indicate antibody binding as described before. Cytospin slides are analyzed with an automated cellular imaging system, such as ChromaVision Medical Systems, Inc., San Juan Capistrano, Calif.

Those skilled in the art will recognize, or be able to ascertain using no more than routine experimentation, many equivalents to the specific embodiments of the invention described herein. Such equivalents are intended to be encompassed by the following claims.

We claim:

1. An isolated antibody comprising a variable light (VL) chain region comprising the amino acid sequence of SEQ ID NO: 5, wherein the antibody binds specifically to Notch3.

2. An isolated antibody comprising a variable heavy (VH) chain region comprising the amino acid sequence of SEQ ID NO: 4, wherein the antibody binds specifically to Notch3.

3. The antibody of claim 1, further comprising a variable heavy (VH) chain region comprising the amino acid sequence of SEQ ID NO: 4.

4. An isolated antibody comprising a variable heavy (VH) chain region comprising complementarity determining regions (CDRs) of SEQ ID NO: 14, 15, and 16, wherein the antibody binds specifically to Notch3.

5. An isolated antibody comprising a variable light (VL) chain region comprising complementarity determining regions (CDRs) of SEQ ID NO: 17, 18, and 19, wherein the antibody binds specifically to Notch3.

6. The antibody of claim 4, further comprising a variable light (VL) chain region comprising CDRs of SEQ ID NO: 17, 18, and 19.

7. The antibody of any of claims 1-3, 4-5, and 6, wherein the antibody is an antibody fragment.

8. The antibody of claim 7, wherein the antibody is a single chain Fv.

9. The antibody of any of claims 1-3, 4-5, and 6, further comprising a label.

\* \* \* \* \*

SEQUENCE LISTING

```
<160> NUMBER OF SEQ ID NOS: 25

<210> SEQ ID NO 1
<211> LENGTH: 2321
<212> TYPE: PRT
<213> ORGANISM: Homo sapiens

<400> SEQUENCE: 1

Met Gly Pro Gly Ala Arg Gly Arg Arg Arg Arg Arg Pro Met Ser
1               5                   10                  15

Pro Pro Pro Pro Pro Pro Val Arg Ala Leu Pro Leu Leu Leu Leu
                20                  25                  30

Leu Ala Gly Pro Gly Ala Ala Ala Pro Pro Cys Leu Asp Gly Ser Pro
            35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
            100                 105                 110

Arg Gly Pro Asp Cys Ser Leu Pro Asp Pro Cys Leu Ser Ser Pro Cys
        115                 120                 125

Ala His Gly Ala Arg Cys Ser Val Gly Pro Asp Gly Arg Phe Leu Cys
    130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
                165                 170                 175
```

```
Thr Pro Gly Ser Phe Arg Cys Gln Cys Pro Ala Gly Tyr Thr Gly Pro
            180                 185                 190

Leu Cys Glu Asn Pro Ala Val Pro Cys Ala Pro Ser Pro Cys Arg Asn
            195                 200                 205

Gly Gly Thr Cys Arg Gln Ser Gly Asp Leu Thr Tyr Asp Cys Ala Cys
210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
            245                 250                 255

Thr Tyr Asn Cys Gln Cys Pro Pro Glu Trp Thr Gly Gln Phe Cys Thr
            260                 265                 270

Glu Asp Val Asp Glu Cys Gln Leu Gln Pro Asn Ala Cys His Asn Gly
            275                 280                 285

Gly Thr Cys Phe Asn Thr Leu Gly Gly His Ser Cys Val Cys Val Asn
            290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
            325                 330                 335

Tyr Cys Ala Cys Pro Met Gly Lys Thr Gly Leu Leu Cys His Leu Asp
            340                 345                 350

Asp Ala Cys Val Ser Asn Pro Cys His Glu Asp Ala Ile Cys Asp Thr
            355                 360                 365

Asn Pro Val Asn Gly Arg Ala Ile Cys Thr Cys Pro Pro Gly Phe Thr
370                 375                 380

Gly Gly Ala Cys Asp Gln Asp Val Asp Glu Cys Ser Ile Gly Ala Asn
385                 390                 395                 400

Pro Cys Glu His Leu Gly Arg Cys Val Asn Thr Gln Gly Ser Phe Leu
            405                 410                 415

Cys Gln Cys Gly Arg Gly Tyr Thr Gly Pro Arg Cys Glu Thr Asp Val
            420                 425                 430

Asn Glu Cys Leu Ser Gly Pro Cys Arg Asn Gln Ala Thr Cys Leu Asp
            435                 440                 445

Arg Ile Gly Gln Phe Thr Cys Ile Cys Met Ala Gly Phe Thr Gly Thr
            450                 455                 460

Tyr Cys Glu Val Asp Ile Asp Glu Cys Gln Ser Ser Pro Cys Val Asn
465                 470                 475                 480

Gly Gly Val Cys Lys Asp Arg Val Asn Gly Phe Ser Cys Thr Cys Pro
            485                 490                 495

Ser Gly Phe Ser Gly Ser Thr Cys Gln Leu Asp Val Asp Glu Cys Ala
            500                 505                 510

Ser Thr Pro Cys Arg Asn Gly Ala Lys Cys Val Asp Gln Pro Asp Gly
            515                 520                 525

Tyr Glu Cys Arg Cys Ala Glu Gly Phe Glu Gly Thr Leu Cys Asp Arg
            530                 535                 540

Asn Val Asp Asp Cys Ser Pro Asp Pro Cys His His Gly Arg Cys Val
545                 550                 555                 560

Asp Gly Ile Ala Ser Phe Ser Cys Ala Cys Ala Pro Gly Tyr Thr Gly
            565                 570                 575

Thr Arg Cys Glu Ser Gln Val Asp Glu Cys Arg Ser Gln Pro Cys Arg
            580                 585                 590

His Gly Gly Lys Cys Leu Asp Leu Val Asp Lys Tyr Leu Cys Arg Cys
            595                 600                 605
```

-continued

```
Pro Ser Gly Thr Thr Gly Val Asn Cys Glu Val Asn Ile Asp Asp Cys
        610                 615                 620

Ala Ser Asn Pro Cys Thr Phe Gly Val Cys Arg Asp Gly Ile Asn Arg
625                 630                 635                 640

Tyr Asp Cys Val Cys Gln Pro Gly Phe Thr Gly Pro Leu Cys Asn Val
                    645                 650                 655

Glu Ile Asn Glu Cys Ala Ser Ser Pro Cys Gly Glu Gly Ser Cys
                660                 665                 670

Val Asp Gly Glu Asn Gly Phe Arg Cys Leu Cys Pro Pro Gly Ser Leu
            675                 680                 685

Pro Pro Leu Cys Leu Pro Ser His Pro Cys Ala His Glu Pro Cys
690                 695                 700

Ser His Gly Ile Cys Tyr Asp Ala Pro Gly Gly Phe Arg Cys Val Cys
705                 710                 715                 720

Glu Pro Gly Trp Ser Gly Pro Arg Cys Ser Gln Ser Leu Ala Arg Asp
                725                 730                 735

Ala Cys Glu Ser Gln Pro Cys Arg Ala Gly Gly Thr Cys Ser Ser Asp
                740                 745                 750

Gly Met Gly Phe His Cys Thr Cys Pro Pro Gly Val Gln Gly Arg Gln
            755                 760                 765

Cys Glu Leu Leu Ser Pro Cys Thr Pro Asn Pro Cys Glu His Gly Gly
770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Asp Val Asp Glu Cys Ala Gly
                805                 810                 815

Pro Ala Pro Cys Gly Pro His Gly Ile Cys Thr Asn Leu Ala Gly Ser
                820                 825                 830

Phe Ser Cys Thr Cys His Gly Gly Tyr Thr Gly Pro Ser Cys Asp Gln
            835                 840                 845

Asp Ile Asn Asp Cys Asp Pro Asn Pro Cys Leu Asn Gly Gly Ser Cys
                850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
                900                 905                 910

Pro Pro Gly Tyr Gly Gly Phe His Cys Glu Gln Asp Leu Pro Asp Cys
            915                 920                 925

Ser Pro Ser Ser Cys Phe Asn Gly Gly Thr Cys Val Asp Gly Val Asn
930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
        995                 1000                1005

Cys Gln Asn Gly Gly Arg Cys Val Gln Thr Gly Ala Tyr Cys Leu
        1010                1015                1020

Cys Pro Pro Gly Trp Ser Gly Arg Leu Cys Asp Ile Arg Ser Leu
        1025                1030                1035
```

-continued

Pro Cys Arg Glu Ala Ala Gln Ile Gly Val Arg Leu Glu Gln
1040                1045                1050

Leu Cys Gln Ala Gly Gly Gln Cys Val Asp Glu Asp Ser Ser His
    1055                1060                1065

Tyr Cys Val Cys Pro Glu Gly Arg Thr Gly Ser His Cys Glu Gln
    1070                1075                1080

Glu Val Asp Pro Cys Leu Ala Gln Pro Cys Gln His Gly Gly Thr
    1085                1090                1095

Cys Arg Gly Tyr Met Gly Gly Tyr Met Cys Glu Cys Leu Pro Gly
    1100                1105                1110

Tyr Asn Gly Asp Asn Cys Glu Asp Asp Val Asp Glu Cys Ala Ser
    1115                1120                1125

Gln Pro Cys Gln His Gly Gly Ser Cys Ile Asp Leu Val Ala Arg
    1130                1135                1140

Tyr Leu Cys Ser Cys Pro Pro Gly Thr Leu Gly Val Leu Cys Glu
    1145                1150                1155

Ile Asn Glu Asp Asp Cys Gly Pro Gly Pro Pro Leu Asp Ser Gly
    1160                1165                1170

Pro Arg Cys Leu His Asn Gly Thr Cys Val Asp Leu Val Gly Gly
    1175                1180                1185

Phe Arg Cys Thr Cys Pro Pro Gly Tyr Thr Gly Leu Arg Cys Glu
    1190                1195                1200

Ala Asp Ile Asn Glu Cys Arg Ser Gly Ala Cys His Ala Ala His
    1205                1210                1215

Thr Arg Asp Cys Leu Gln Asp Pro Gly Gly Gly Phe Arg Cys Leu
    1220                1225                1230

Cys His Ala Gly Phe Ser Gly Pro Arg Cys Gln Thr Val Leu Ser
    1235                1240                1245

Pro Cys Glu Ser Gln Pro Cys Gln His Gly Gly Gln Cys Arg Pro
    1250                1255                1260

Ser Pro Gly Pro Gly Gly Gly Leu Thr Phe Thr Cys His Cys Ala
    1265                1270                1275

Gln Pro Phe Trp Gly Pro Arg Cys Glu Arg Val Ala Arg Ser Cys
    1280                1285                1290

Arg Glu Leu Gln Cys Pro Val Gly Val Pro Cys Gln Gln Thr Pro
    1295                1300                1305

Arg Gly Pro Arg Cys Ala Cys Pro Pro Gly Leu Ser Gly Pro Ser
    1310                1315                1320

Cys Arg Ser Phe Pro Gly Ser Pro Pro Gly Ala Ser Asn Ala Ser
    1325                1330                1335

Cys Ala Ala Ala Pro Cys Leu His Gly Gly Ser Cys Arg Pro Ala
    1340                1345                1350

Pro Leu Ala Pro Phe Phe Arg Cys Ala Cys Ala Gln Gly Trp Thr
    1355                1360                1365

Gly Pro Arg Cys Glu Ala Pro Ala Ala Ala Pro Glu Val Ser Glu
    1370                1375                1380

Glu Pro Arg Cys Pro Arg Ala Ala Cys Gln Ala Lys Arg Gly Asp
    1385                1390                1395

Gln Arg Cys Asp Arg Glu Cys Asn Ser Pro Gly Cys Gly Trp Asp
    1400                1405                1410

Gly Gly Asp Cys Ser Leu Ser Val Gly Asp Pro Trp Arg Gln Cys
    1415                1420                1425

Glu Ala Leu Gln Cys Trp Arg Leu Phe Asn Asn Ser Arg Cys Asp
    1430                1435                1440

-continued

```
Pro Ala Cys Ser Ser Pro Ala Cys Leu Tyr Asp Asn Phe Asp Cys
    1445            1450                1455

His Ala Gly Gly Arg Glu Arg Thr Cys Asn Pro Val Tyr Glu Lys
    1460            1465                1470

Tyr Cys Ala Asp His Phe Ala Asp Gly Arg Cys Asp Gln Gly Cys
    1475            1480                1485

Asn Thr Glu Glu Cys Gly Trp Asp Gly Leu Asp Cys Ala Ser Glu
    1490            1495                1500

Val Pro Ala Leu Leu Ala Arg Gly Val Leu Val Leu Thr Val Leu
    1505            1510                1515

Leu Pro Pro Glu Glu Leu Leu Arg Ser Ser Ala Asp Phe Leu Gln
    1520            1525                1530

Arg Leu Ser Ala Ile Leu Arg Thr Ser Leu Arg Phe Arg Leu Asp
    1535            1540                1545

Ala His Gly Gln Ala Met Val Phe Pro Tyr His Arg Pro Ser Pro
    1550            1555                1560

Gly Ser Glu Pro Arg Ala Arg Arg Glu Leu Ala Pro Glu Val Ile
    1565            1570                1575

Gly Ser Val Val Met Leu Glu Ile Asp Asn Arg Leu Cys Leu Gln
    1580            1585                1590

Ser Pro Glu Asn Asp His Cys Phe Pro Asp Ala Gln Ser Ala Ala
    1595            1600                1605

Asp Tyr Leu Gly Ala Leu Ser Ala Val Glu Arg Leu Asp Phe Pro
    1610            1615                1620

Tyr Pro Leu Arg Asp Val Arg Gly Glu Pro Leu Glu Pro Pro Glu
    1625            1630                1635

Pro Ser Val Pro Leu Leu Pro Leu Leu Val Ala Gly Ala Val Leu
    1640            1645                1650

Leu Leu Val Ile Leu Val Leu Gly Val Met Val Ala Arg Arg Lys
    1655            1660                1665

Arg Glu His Ser Thr Leu Trp Phe Pro Glu Gly Phe Ser Leu His
    1670            1675                1680

Lys Asp Val Ala Ser Gly His Lys Gly Arg Arg Glu Pro Val Gly
    1685            1690                1695

Gln Asp Ala Leu Gly Met Lys Asn Met Ala Lys Gly Glu Ser Leu
    1700            1705                1710

Met Gly Glu Val Ala Thr Asp Trp Met Asp Thr Glu Cys Pro Glu
    1715            1720                1725

Ala Lys Arg Leu Lys Val Glu Pro Gly Met Gly Ala Glu Glu
    1730            1735                1740

Ala Val Asp Cys Arg Gln Trp Thr Gln His His Leu Val Ala Ala
    1745            1750                1755

Asp Ile Arg Val Ala Pro Ala Met Ala Leu Thr Pro Pro Gln Gly
    1760            1765                1770

Asp Ala Asp Ala Asp Gly Met Asp Val Asn Val Arg Gly Pro Asp
    1775            1780                1785

Gly Phe Thr Pro Leu Met Leu Ala Ser Phe Cys Gly Gly Ala Leu
    1790            1795                1800

Glu Pro Met Pro Thr Glu Glu Asp Glu Ala Asp Asp Thr Ser Ala
    1805            1810                1815

Ser Ile Ile Ser Asp Leu Ile Cys Gln Gly Ala Gln Leu Gly Ala
    1820            1825                1830

Arg Thr Asp Arg Thr Gly Glu Thr Ala Leu His Leu Ala Ala Arg
    1835            1840                1845
```

```
Tyr Ala Arg Ala Asp Ala Ala Lys Arg Leu Leu Asp Ala Gly Ala
    1850                1855                1860

Asp Thr Asn Ala Gln Asp His Ser Gly Arg Thr Pro Leu His Thr
    1865                1870                1875

Ala Val Thr Ala Asp Ala Gln Gly Val Phe Gln Ile Leu Ile Arg
    1880                1885                1890

Asn Arg Ser Thr Asp Leu Asp Ala Arg Met Ala Asp Gly Ser Thr
    1895                1900                1905

Ala Leu Ile Leu Ala Ala Arg Leu Ala Val Glu Gly Met Val Glu
    1910                1915                1920

Glu Leu Ile Ala Ser His Ala Asp Val Asn Ala Val Asp Glu Leu
    1925                1930                1935

Gly Lys Ser Ala Leu His Trp Ala Ala Ala Val Asn Asn Val Glu
    1940                1945                1950

Ala Thr Leu Ala Leu Leu Lys Asn Gly Ala Asn Lys Asp Met Gln
    1955                1960                1965

Asp Ser Lys Glu Glu Thr Pro Leu Phe Leu Ala Ala Arg Glu Gly
    1970                1975                1980

Ser Tyr Glu Ala Ala Lys Leu Leu Leu Asp His Phe Ala Asn Arg
    1985                1990                1995

Glu Ile Thr Asp His Leu Asp Arg Leu Pro Arg Asp Val Ala Gln
    2000                2005                2010

Glu Arg Leu His Gln Asp Ile Val Arg Leu Leu Asp Gln Pro Ser
    2015                2020                2025

Gly Pro Arg Ser Pro Pro Gly Pro His Gly Leu Gly Pro Leu Leu
    2030                2035                2040

Cys Pro Pro Gly Ala Phe Leu Pro Gly Leu Lys Ala Ala Gln Ser
    2045                2050                2055

Gly Ser Lys Lys Ser Arg Arg Pro Pro Gly Lys Ala Gly Leu Gly
    2060                2065                2070

Pro Gln Gly Pro Arg Gly Arg Gly Lys Lys Leu Thr Leu Ala Cys
    2075                2080                2085

Pro Gly Pro Leu Ala Asp Ser Ser Val Thr Leu Ser Pro Val Asp
    2090                2095                2100

Ser Leu Asp Ser Pro Arg Pro Phe Gly Gly Pro Pro Ala Ser Pro
    2105                2110                2115

Gly Gly Phe Pro Leu Glu Gly Pro Tyr Ala Ala Ala Thr Ala Thr
    2120                2125                2130

Ala Val Ser Leu Ala Gln Leu Gly Gly Pro Gly Arg Ala Gly Leu
    2135                2140                2145

Gly Arg Gln Pro Pro Gly Gly Cys Val Leu Ser Leu Gly Leu Leu
    2150                2155                2160

Asn Pro Val Ala Val Pro Leu Asp Trp Ala Arg Leu Pro Pro Pro
    2165                2170                2175

Ala Pro Pro Gly Pro Ser Phe Leu Leu Pro Leu Ala Pro Gly Pro
    2180                2185                2190

Gln Leu Leu Asn Pro Gly Thr Pro Val Ser Pro Gln Glu Arg Pro
    2195                2200                2205

Pro Pro Tyr Leu Ala Val Pro Gly His Gly Glu Glu Tyr Pro Val
    2210                2215                2220

Ala Gly Ala His Ser Ser Pro Pro Lys Ala Arg Phe Leu Arg Val
    2225                2230                2235

Pro Ser Glu His Pro Tyr Leu Thr Pro Ser Pro Glu Ser Pro Glu
    2240                2245                2250
```

```
His Trp Ala Ser Pro Ser Pro Ser Leu Ser Asp Trp Ser Glu
    2255            2260                2265

Ser Thr Pro Ser Pro Ala Thr Ala Thr Gly Ala Met Ala Thr Thr
    2270            2275            2280

Thr Gly Ala Leu Pro Ala Gln Pro Leu Pro Leu Ser Val Pro Ser
    2285            2290            2295

Ser Leu Ala Gln Ala Gln Thr Gln Leu Gly Pro Gln Pro Glu Val
    2300            2305            2310

Thr Pro Lys Arg Gln Val Leu Ala
    2315            2320

<210> SEQ ID NO 2
<211> LENGTH: 123
<212> TYPE: PRT
<213> ORGANISM: Artificial
<220> FEATURE:
<223> OTHER INFORMATION: Heavy chain variable region derived from mAb
      255A-71

<400> SEQUENCE: 2

Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Lys Leu Glu
        35                  40                  45

Trp Met Gly Phe Ile Ser Tyr Asp Gly Ser Asn Asn Tyr Asn Pro Ser
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Ala Thr Phe Tyr
                85                  90                  95

Cys Ala Thr Leu Tyr Tyr Asp Tyr Asp Gly Asn Tyr Phe Asp Tyr Trp
            100                 105                 110

Gly Gln Gly Thr Thr Leu Thr Val Ser Ser Ala
        115                 120

<210> SEQ ID NO 3
<211> LENGTH: 116
<212> TYPE: PRT
<213> ORGANISM: Artificial
<220> FEATURE:
<223> OTHER INFORMATION: Light chain variable region derived from mAb
      255A-71

<400> SEQUENCE: 3

Cys Asp Ile Gln Met Thr Gln Thr Thr Ser Ser Leu Ser Ala Ser Leu
1               5                   10                  15

Gly Asp Arg Val Thr Ile Ser Cys Arg Thr Ser Gln Asp Ile Ser Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Ala Leu Pro
                85                  90                  95
```

Leu Thr Phe Gly Pro Gly Thr Lys Leu Glu Leu Lys Arg Ala Asp Ala
            100                 105                 110

Ala Pro Thr Val
        115

<210> SEQ ID NO 4
<211> LENGTH: 120
<212> TYPE: PRT
<213> ORGANISM: Artificial
<220> FEATURE:
<223> OTHER INFORMATION: Heavy chain variable region derived from mAb
      255A-77

<400> SEQUENCE: 4

Cys Gln Val Gln Leu Gln Gln Ser Gly Asp Asp Leu Val Lys Pro Gly
1               5                   10                  15

Ala Ser Val Lys Leu Ser Cys Lys Ala Ser Gly Tyr Thr Phe Thr Ser
            20                  25                  30

Tyr Trp Ile Asn Trp Ile Lys Gln Arg Pro Gly Gln Gly Leu Glu Trp
        35                  40                  45

Ile Gly His Ile Gly Pro Gly Ser Gly Ser Thr Tyr Tyr Asn Glu Ile
    50                  55                  60

Phe Lys Gly Lys Ala Thr Leu Thr Val Asp Thr Ser Ser Ser Thr Ala
65                  70                  75                  80

Tyr Ile Gln Leu Ser Ser Leu Ser Ser Glu Asp Ser Ala Val Tyr Phe
                85                  90                  95

Cys Val Leu Thr Arg Tyr Phe Tyr Ala Met Asp Tyr Trp Gly Gln Gly
            100                 105                 110

Thr Ser Val Thr Val Ser Ser Ala
        115                 120

<210> SEQ ID NO 5
<211> LENGTH: 123
<212> TYPE: PRT
<213> ORGANISM: Artificial
<220> FEATURE:
<223> OTHER INFORMATION: Light chain variable region derived from
      255A-77

<400> SEQUENCE: 5

Asp Ile Val Met Thr Gln Ser Pro Ser Ser Leu Ala Val Thr Ala Gly
1               5                   10                  15

Glu Lys Val Thr Met Arg Cys Lys Ser Ser Gln Ser Leu Leu Trp Ser
            20                  25                  30

Val Asn Gln Asn Asn Tyr Leu Ser Trp Tyr Gln Gln Lys Gln Gly Gln
        35                  40                  45

Pro Pro Lys Leu Leu Ile Tyr Gly Ala Ser Ile Arg Glu Ser Trp Val
    50                  55                  60

Pro Asp Arg Phe Thr Gly Ser Gly Ser Gly Thr Asp Phe Thr Leu Thr
65                  70                  75                  80

Ile Ser Asn Val His Val Glu Asp Leu Ala Val Tyr Tyr Cys Gln His
                85                  90                  95

Asn His Gly Ser Phe Leu Pro Leu Thr Phe Gly Ala Gly Thr Lys Leu
            100                 105                 110

Glu Leu Lys Arg Ala Asp Ala Ala Pro Thr Val
        115                 120

```
<210> SEQ ID NO 6
<211> LENGTH: 121
<212> TYPE: PRT
<213> ORGANISM: Artificial
<220> FEATURE:
<223> OTHER INFORMATION: Heavy chain variable region derived from
      256A-13

<400> SEQUENCE: 6

Ser Gln Val Gln Leu Gln Gln Ser Gly Ala Glu Leu Ala Lys Pro Gly
1               5                   10                  15

Thr Ser Val Lys Met Ala Cys Lys Ala Ser Gly Tyr Thr Phe Thr Thr
            20                  25                  30

His Trp Met Asn Trp Val Lys Gln Arg Pro Gly Gln Gly Leu Glu Trp
        35                  40                  45

Ile Gly Thr Ile Asn Pro Ser Asn Asp Phe Thr Asp Cys Asn Gln Lys
    50                  55                  60

Phe Lys Asp Lys Ala Ile Leu Thr Ala Asp Lys Ser Ser Ser Thr Ala
65                  70                  75                  80

Tyr Met Gln Leu Ser Ser Leu Thr Ser Glu Asp Ser Ala Ile Tyr Tyr
                85                  90                  95

Cys Ala Ser Gly Leu Thr Ala Arg Ala Trp Phe Ala Tyr Trp Gly Gln
            100                 105                 110

Gly Thr Leu Val Thr Val Ser Ala Ala
        115                 120

<210> SEQ ID NO 7
<211> LENGTH: 102
<212> TYPE: PRT
<213> ORGANISM: Artificial
<220> FEATURE:
<223> OTHER INFORMATION: Light chain variable region derived from
      256A-13

<400> SEQUENCE: 7

Arg Ala Thr Ile Ser Cys Arg Ala Ser Gln Ser Val Thr Thr Ser Asn
1               5                   10                  15

Tyr Ser Tyr Met His Trp Phe Gln Gln Lys Pro Gly Gln Pro Pro Lys
            20                  25                  30

Leu Leu Ile Lys Tyr Ala Ser Asn Leu Asp Ser Gly Val Pro Ala Arg
        35                  40                  45

Phe Ser Gly Ser Gly Ser Gly Thr Asp Phe Thr Leu Asn Ile His Pro
    50                  55                  60

Val Glu Glu Glu Asp Thr Ala Thr Phe Tyr Cys Gln His Ser Trp Glu
65                  70                  75                  80

Ile Pro Tyr Thr Phe Gly Gly Gly Thr Asn Leu Glu Ile Lys Arg Ala
                85                  90                  95

Asp Ala Ala Pro Thr Val
            100

<210> SEQ ID NO 8
<211> LENGTH: 12
<212> TYPE: PRT
<213> ORGANISM: Artificial
<220> FEATURE:
<223> OTHER INFORMATION: CDR-H1 derived from the heavy chain variable
      region of mAb 255A-71

<400> SEQUENCE: 8

Gly Tyr Ser Ile Thr Ser Gly Tyr Tyr Trp Asn Trp
1               5                   10
```

```
<210> SEQ ID NO 9
<211> LENGTH: 10
<212> TYPE: PRT
<213> ORGANISM: Artificial
<220> FEATURE:
<223> OTHER INFORMATION: CDR-H2 derived from the heavy chain variable
      region of mAb 255A-71

<400> SEQUENCE: 9

Ile Ser Tyr Asp Gly Ser Asn Asn Tyr Asn
1               5                   10

<210> SEQ ID NO 10
<211> LENGTH: 12
<212> TYPE: PRT
<213> ORGANISM: Artificial
<220> FEATURE:
<223> OTHER INFORMATION: CDR-H3 derived from the heavy chain variable
      region of mAb 255A-71

<400> SEQUENCE: 10

Leu Tyr Tyr Asp Tyr Asp Gly Asn Tyr Phe Asp Tyr
1               5                   10

<210> SEQ ID NO 11
<211> LENGTH: 11
<212> TYPE: PRT
<213> ORGANISM: Artificial
<220> FEATURE:
<223> OTHER INFORMATION: CDR-L1 derived from the heavy chain variable
      region of mAb 255A-71

<400> SEQUENCE: 11

Arg Thr Ser Gln Asp Ile Ser Asn Tyr Leu Asn
1               5                   10

<210> SEQ ID NO 12
<211> LENGTH: 7
<212> TYPE: PRT
<213> ORGANISM: Artificial
<220> FEATURE:
<223> OTHER INFORMATION: CDR-L2 derived from the heavy chain variable
      region of mAb 255A-71

<400> SEQUENCE: 12

Tyr Thr Ser Arg Leu His Ser
1               5

<210> SEQ ID NO 13
<211> LENGTH: 8
<212> TYPE: PRT
<213> ORGANISM: Artificial
<220> FEATURE:
<223> OTHER INFORMATION: CDR-L3 derived from the heavy chain variable
      region of mAb 255A-71

<400> SEQUENCE: 13

Gln Gln Gly Asn Ala Leu Pro Thr
1               5

<210> SEQ ID NO 14
<211> LENGTH: 10
<212> TYPE: PRT
<213> ORGANISM: Artificial
<220> FEATURE:
<223> OTHER INFORMATION: CDR-H1 derived from the heavy chain variable
      region of mAb 255A-77
```

```
<400> SEQUENCE: 14

Gly Tyr Thr Phe Thr Ser Tyr Trp Ile Asn
1               5                   10

<210> SEQ ID NO 15
<211> LENGTH: 12
<212> TYPE: PRT
<213> ORGANISM: Artificial
<220> FEATURE:
<223> OTHER INFORMATION: CDR-H2 derived from the heavy chain variable
      region of mAb 255A-77

<400> SEQUENCE: 15

His Ile Gly Pro Gly Ser Gly Ser Thr Tyr Tyr Asn
1               5                   10

<210> SEQ ID NO 16
<211> LENGTH: 9
<212> TYPE: PRT
<213> ORGANISM: Artificial
<220> FEATURE:
<223> OTHER INFORMATION: CDR-H3 derived from the heavy chain variable
      region of mAb 255A-77

<400> SEQUENCE: 16

Thr Arg Tyr Phe Tyr Ala Met Asp Tyr
1               5

<210> SEQ ID NO 17
<211> LENGTH: 17
<212> TYPE: PRT
<213> ORGANISM: Artificial
<220> FEATURE:
<223> OTHER INFORMATION: CDR-L1 derived from the heavy chain variable
      region of mAb 255A-77

<400> SEQUENCE: 17

Lys Ser Ser Gln Ser Leu Leu Trp Ser Val Asn Gln Asn Asn Tyr Leu
1               5                   10                  15

Ser

<210> SEQ ID NO 18
<211> LENGTH: 7
<212> TYPE: PRT
<213> ORGANISM: Artificial
<220> FEATURE:
<223> OTHER INFORMATION: CDR-L2 derived from the heavy chain variable
      region of mAb 255A-77

<400> SEQUENCE: 18

Gly Ala Ser Ile Arg Glu Ser
1               5

<210> SEQ ID NO 19
<211> LENGTH: 11
<212> TYPE: PRT
<213> ORGANISM: Artificial
<220> FEATURE:
<223> OTHER INFORMATION: CDR-L3 derived from the heavy chain variable
      region of mAb 255A-77

<400> SEQUENCE: 19

Gln His Asn His Gly Ser Phe Leu Pro Leu Thr
1               5                   10
```

-continued

```
<210> SEQ ID NO 20
<211> LENGTH: 11
<212> TYPE: PRT
<213> ORGANISM: Artificial
<220> FEATURE:
<223> OTHER INFORMATION: CDR-H1 derived from the heavy chain varible
      region of mAb 256A-13

<400> SEQUENCE: 20

Gly Tyr Thr Phe Thr Thr His Trp Met Asn Trp
1               5                   10

<210> SEQ ID NO 21
<211> LENGTH: 11
<212> TYPE: PRT
<213> ORGANISM: Artificial
<220> FEATURE:
<223> OTHER INFORMATION: CDR-H2 derived from the heavy chain varible
      region of mAb 256A-13

<400> SEQUENCE: 21

Ile Asn Pro Ser Asn Asp Phe Thr Asp Cys Asn
1               5                   10

<210> SEQ ID NO 22
<211> LENGTH: 8
<212> TYPE: PRT
<213> ORGANISM: Artificial
<220> FEATURE:
<223> OTHER INFORMATION: CDR-H3 derived from the heavy chain varible
      region of mAb 256A-13

<400> SEQUENCE: 22

Thr Ala Arg Ala Trp Phe Ala Tyr
1               5

<210> SEQ ID NO 23
<211> LENGTH: 15
<212> TYPE: PRT
<213> ORGANISM: Artificial
<220> FEATURE:
<223> OTHER INFORMATION: CDR-L1 derived from the heavy chain varible
      region of mAb 256A-13

<400> SEQUENCE: 23

Arg Ala Ser Gln Ser Val Thr Thr Ser Asn Tyr Ser Tyr Met His
1               5                   10                  15

<210> SEQ ID NO 24
<211> LENGTH: 8
<212> TYPE: PRT
<213> ORGANISM: Artificial
<220> FEATURE:
<223> OTHER INFORMATION: CDR-L2 derived from the heavy chain varible
      region of mAb 256A-13

<400> SEQUENCE: 24

Tyr Ala Ser Asn Leu Asp Ser Gly
1               5

<210> SEQ ID NO 25
<211> LENGTH: 9
<212> TYPE: PRT
<213> ORGANISM: Artificial
<220> FEATURE:
<223> OTHER INFORMATION: CDR-L3 derived from the heavy chain varible
      region of mAb 256A-13
```

-continued

```
<400> SEQUENCE: 25

Gln His Ser Trp Glu Ile Pro Tyr Thr
1               5
```